United States Patent
Krenik

(10) Patent No.: US 10,179,081 B2
(45) Date of Patent: *Jan. 15, 2019

(54) VISION MEASUREMENT AND TRAINING SYSTEM AND METHOD OF OPERATION THEREOF

(71) Applicant: VITAL ART AND SCIENCE, LLC, Richardson, TX (US)

(72) Inventor: William R. Krenik, Richardson, TX (US)

(73) Assignee: VITAL ART AND SCIENCE, LLC, Richardson, TX (US)

( * ) Notice: Subject to any disclaimer, the term of this patent is extended or adjusted under 35 U.S.C. 154(b) by 106 days.

This patent is subject to a terminal disclaimer.

(21) Appl. No.: 14/928,129

(22) Filed: Oct. 30, 2015

(65) Prior Publication Data

US 2016/0045388 A1    Feb. 18, 2016

Related U.S. Application Data

(63) Continuation of application No. 14/203,080, filed on Mar. 10, 2014, now Pat. No. 9,186,293, which is a
(Continued)

(51) Int. Cl.
*A61B 3/00* (2006.01)
*A61H 5/00* (2006.01)
(Continued)

(52) U.S. Cl.
CPC ............ *A61H 5/005* (2013.01); *A61B 3/0033* (2013.01); *A61B 3/024* (2013.01); *A61B 3/032* (2013.01); *A61B 3/036* (2013.01); *A61B 3/08* (2013.01); *A61H 23/02* (2013.01); *A61H 2201/0207* (2013.01); *A61H 2201/10* (2013.01); *A61H 2201/1604* (2013.01); *A61H 2201/165* (2013.01); *A61H 2201/501* (2013.01);
(Continued)

(58) Field of Classification Search
CPC ....... A61B 3/0033; A61B 3/0083; A61B 3/02; A61B 3/024; A61B 3/032; A61B 3/036; A61B 3/08; A61H 5/00
USPC ....... 351/201, 202, 203, 222, 223, 224, 237, 351/240
See application file for complete search history.

(56) References Cited

U.S. PATENT DOCUMENTS 4,403,840 A    9/1983 Okun
4,561,723 A    12/1985 Hamano et al.
(Continued)

*Primary Examiner* — Dawayne A Pinkney

(57) ABSTRACT

One aspect of the disclosure provides a binocular viewing system. In one embodiment, the binocular viewing system includes a binocular viewer and a computer. The binocular viewer has left and right display screens and a variable focal depth optical subsystem located in an optical path between and separate from the display screens and a user when the user uses the binocular viewer. The computer is configured to provide control signals to the binocular viewer. The control signals are operable to place images on the left and right display screens and vary a focal depth of the variable focal depth optical subsystem. The images include a plurality of objects controlled by the variable focal depth optical subsystem to make at least one of the plurality of objects appear closer to the user and at least one of another of said plurality of objects appear farther away from the user.

14 Claims, 19 Drawing Sheets

Related U.S. Application Data continuation of application No. 11/679,564, filed on Feb. 27, 2007, now Pat. No. 8,668,334.

(51) Int. Cl.

| | | |
|---|---|---|
| *A61B 3/08* | (2006.01) | |
| *A61B 3/032* | (2006.01) | |
| *A61B 3/036* | (2006.01) | |
| *A61B 3/024* | (2006.01) | |
| *A61H 23/02* | (2006.01) | |

(52) U.S. Cl.
CPC .......... *A61H 2201/5043* (2013.01); *A61H 2201/5048* (2013.01); *A61H 2201/5058* (2013.01); *A61H 2201/5092* (2013.01); *A61H 2201/5097* (2013.01)

(56) References Cited

U.S. PATENT DOCUMENTS

| | | | |
|---|---|---|---|
| 4,756,305 A | 7/1988 | Mateik et al. | |
| 4,863,258 A | 9/1989 | Greene | |
| 5,051,931 A | 9/1991 | Cheu et al. | |
| 5,088,810 A | 2/1992 | Galanter et al. | |
| 5,173,724 A | 12/1992 | Bonham et al. | |
| 5,515,069 A | 5/1996 | Dillon, III | |
| 5,539,481 A | 7/1996 | Vax | |
| 5,550,602 A * | 8/1996 | Braeuning | A61B 3/024 348/E13.033 |
| 5,589,897 A | 12/1996 | Sinclair et al. | |
| 5,645,513 A | 7/1997 | Haydocy et al. | |
| 5,646,710 A | 7/1997 | Caskey | |
| 5,737,060 A | 4/1998 | Kasha, Jr. | |
| 5,781,274 A | 7/1998 | Moreno | |
| 5,861,936 A | 1/1999 | Sorensen | |
| 5,864,384 A | 1/1999 | Mcclure et al. | |
| 5,956,128 A | 9/1999 | Itojima et al. | |
| 6,033,076 A | 3/2000 | Braeuning et al. | |
| 6,042,231 A | 3/2000 | Fateh | |
| 6,139,149 A | 10/2000 | Shafer et al. | |
| 6,260,970 B1 | 7/2001 | Horn | |
| 6,409,513 B1 | 6/2002 | Kawamura et al. | |
| 6,478,425 B2 | 11/2002 | Trajkovic et al. | |
| 6,533,417 B1 | 3/2003 | Sain | |
| 6,568,809 B2 | 5/2003 | Trajkovic et al. | |
| 6,656,131 B2 | 12/2003 | Alster et al. | |
| 6,854,846 B2 | 2/2005 | Quigley | |
| 6,856,131 B2 | 2/2005 | Miyazawa et al. | |
| 7,220,000 B2 | 5/2007 | Alster et al. | |
| 7,275,830 B2 | 10/2007 | Alster et al. | |
| 7,334,892 B2 | 2/2008 | Goodall et al. | |
| 7,665,847 B2 | 2/2010 | Alster et al. | |
| 7,671,888 B2 | 3/2010 | Nogami et al. | |
| 8,668,334 B2 * | 3/2014 | Krenik | A61B 3/032 348/42 |
| 9,039,182 B2 | 5/2015 | Huang | |
| 9,186,293 B2 * | 11/2015 | Krenik | A61B 3/032 |
| 2002/0113943 A1 | 8/2002 | Trajkovic et al. | |
| 2003/0016332 A1 | 1/2003 | Trajkovic et al. | |
| 2005/0007550 A1 | 1/2005 | Turkov et al. | |
| 2005/0213033 A1 | 9/2005 | Sabel | |
| 2005/0264760 A1 * | 12/2005 | Ikezawa | A61B 3/032 351/239 |
| 2006/0012674 A1 | 1/2006 | Kao | |
| 2006/0087618 A1 | 4/2006 | Smart et al. | |
| 2006/0092377 A1 | 5/2006 | Todd et al. | |
| 2006/0164597 A1 | 7/2006 | Hayakawa et al. | |
| 2012/0120051 A1 | 5/2012 | Liu et al. | |
| 2012/0250152 A1 | 10/2012 | Larson et al. | |

* cited by examiner

VISION MEASUREMENT AND TRAINING SYSTEM AND METHOD OF OPERATION THEREOF

CROSS-REFERENCE TO RELATED APPLICATIONS

This application is a continuation of U.S. application Ser. No. 14/203,080 filed on Mar. 10, 2014, entitled "Vision Measurement and Training System and Method of Operation Thereof", which is a continuation of U.S. application Ser. No. 11/679,564, now U.S. Pat. No. 8,668,334 granted to William R. Krenik filed on Feb. 27, 2007 and entitled, "Vision Measurement and Training System and Method of Operation Thereof", which both are commonly owned with this application and incorporated herein by reference in their entirety.

TECHNICAL FIELD OF THE INVENTION

The disclosure is directed, in general, to optical diagnosis and treatment devices and, more particularly, to a vision measurement and training system and a method of operating the same.

BACKGROUND OF THE INVENTION

There is no question that the ability to see clearly is a most treasured and valued human ability. Regrettably, many vision disorders commonly exist. Focusing disorders such as near-sightedness (myopia), far-sightedness (hyperopia) and astigmatism are very common and are normally treated with prescription lenses (eyeglasses or contact lenses) or refractive surgery. Disorders of the muscles that steer the eyeballs and eye alignment disorders such as strabismus and diplopia are also widespread. And finally, retinal disorders such as macular degeneration, diabetic retinopathy and glaucoma affect tens of millions of persons in the U.S. alone.

Given the broad number of vision conditions that affect the population, it is naturally important that measurement and screening capability be available. Of course, a very large number of optometrists and ophthalmologists perform vision screening and diagnosis on a daily basis. These screening and measurement procedures are normally performed in a specialist's office and often include complex and expensive vision measurement instruments and time consuming interaction between the care provider and the patient. Even once they are diagnosed and treated, some vision diseases such as macular degeneration, diabetic retinopathy and glaucoma require ongoing monitoring that demands repeated visits to a specialist to ensure the disease is remaining under control. Consequently, vision measurement and screening systems that reduce cost, improve accuracy, improve convenience for the care provider or the patient or improve vision measurement and screening ability in other ways are highly beneficial. And as noted, since certain eye diseases require ongoing monitoring, automatic systems that can store measurement data, compare it with new measurements and alert patients or care providers if substantial changes have occurred are also highly desirable and beneficial.

While the need for high quality vision measurement and screening systems is very well established and accepted, vision training has been a topic of controversy. Vision training, vision therapy, eye exercise, vision exercise, orthoptics and some other terms have been used as names for techniques that use training techniques to improve vision function through either training of the eye itself, or by training the brain to improve its interpretation of nerve signals from the eye. In this discussion, "vision training" will normally be used to refer to these techniques, but any of the names listed above can be used to refer to them. In the past, some of these therapies have made claims of "miracle cures" for eye disease and, in some cases, no scientific basis or proof of effectiveness has been available. This has lead some to believe that vision training is not effective. However, vision training has been found to be effective when applied appropriately and for appropriate patient conditions under a professional care provider's supervision.

In 1999 the American Academy of Optometry and the American Optometric Association issued a joint policy statement on vision therapy. This statement can be found in its entirety at the American Academy of Optometry website at www.aaopt.org, so it will not be repeated here. However, several excerpts are very enlightening. The policy statement states: "The human visual system is complex . . . . Many visual conditions can be treated effectively with spectacles or contact lenses alone; however, some are most effectively treated with vision therapy. Vision therapy is a sequence of activities individually prescribed and monitored by the doctor to develop efficient visual skills and processing . . . . The use of lens, prisms, filters, occluders, specialized instruments and computer programs is an integral part of vision therapy." And finally, it is noted that the policy statement states that "Research has demonstrated vision therapy can be an effective treatment for:

Ocular motility dysfunctions (eye movement disorders),
Non-strabismic binocular disorders (inefficient eye teaming),
Strabismus (misalignment of the eyes),
Amblyopia (poorly developed vision),
Accommodative disorders (focusing problems), and
Visual information processing disorders, including visual-motor integration and integration with other sensory modalities."

This joint policy statement on vision therapy makes it very clear that vision therapy or training techniques are effective when properly prescribed for patients with conditions appropriate for a specific therapy. Indeed, vision training has become more widely accepted in recent years. The FDA (Food and Drug Administration) has approved a vision training regimen offered by Neurovision Incorporated for the treatment of amblyopia (www.neuro-vision.com). The American Optometric Association website at www.aoa.org explains the use of prisms in the treatment of strabismus and discusses ways to use vision training in treatment of other vision disorders as well. The effectiveness of fixation training (also sometimes called parafovea training or off-foveal training) which is sometimes used to help patients suffering from macular degeneration learn to make the best use of their remaining vision function is also well established (www.aoa.org/documents/CPG-14.pdf provides a summary of treatments for low vision including teaching off-foveal viewing with guided practice techniques).

Hence, it is well established that vision training techniques are effective when appropriate training regimens are prescribed for certain vision disorders. As would be expected, there have been some attempts to produce devices and therapies to provide vision training. Liberman, for example, U.S. Pat. No. 6,742,892 teaches a device with lights at various distances from a user to improve focusing ability. Regrettably, such devices are somewhat cumbersome, have limited or no ability to measure vision function and are rather boring to operate making it difficult to fully engage a patient in the training regimen. This last issue is especially problematic for use with children. Mateik teaches a binocular viewer in U.S. Pat. No. 4,756,305 that includes the ability to interchange prisms and lens to allow for vision training for strabismus treatment and other treatments as well. Regrettably, Mateik's device cannot measure a patient's vision performance nor adapt automatically to create an effective training system. As the lenses are fixed for a given training session, only limited ranges and accommodations are possible. Hence, it is clear that vision training devices that offer improvements over prior art are highly desirable.

Fortunately, computer graphics and gaming technology has now advanced to the level that low cost, highly effective devices for vision diagnosis, tracking and training can be envisioned. Binocular viewers allow each eye to be measured or trained independently or together, advances in variable optics allow for changes in focus to be accommodated, computer generated graphics allow interesting and engaging images to be created and low cost human input devices allow user feedback information to be collected easily concerning how a user is reacting to a given image or sequence of video.

SUMMARY OF THE INVENTION

To address the above-discussed deficiencies of the prior art, the disclosure provides, in one aspect, a binocular viewer. In one embodiment, the binocular viewer has left and right display screens and a variable focal depth optical subsystem located in an optical path between and separate from the display screens and a user when the user uses the binocular viewer.

Another aspect of the disclosure provides a method of using a binocular viewer. In one embodiment, the method includes viewing left and right display screens of the binocular viewer through a variable focal depth optical subsystem associated with and separate from the left and right display screens.

Yet still another aspect of the disclosure provides a binocular viewing system. In one embodiment, the binocular viewing system includes a binocular viewer and a computer. The binocular viewer has left and right display screens and a variable focal depth optical subsystem located in an optical path between and separate from the display screens and a user when the user uses the binocular viewer. The computer is configured to provide control signals to the binocular viewer. The control signals are operable to place images on the left and right display screens and vary a focal depth of the variable focal depth optical subsystem. The images include a plurality of objects controlled by the variable focal depth optical subsystem to make at least one of the plurality of objects appear closer to the user and at least one of another of said plurality of objects appear farther away from the user.

The foregoing has outlined various features of the disclosure so that those skilled in the pertinent art may better understand the detailed description of the disclosure that follows. Additional features of the disclosure will be described hereinafter that form the subject of the claims of the disclosure. Those skilled in the pertinent art should appreciate that they can readily use the disclosed conception and specific embodiment as a basis for designing or modifying other structures for carrying out the same purposes of the disclosure. Those skilled in the pertinent art should also realize that such equivalent constructions do not depart from the scope of the disclosure.

BRIEF DESCRIPTION OF THE DRAWINGS

For a more complete understanding of the disclosure, reference is now made to the following descriptions taken in conjunction with the accompanying drawings, in which.

DETAILED DESCRIPTION

Figure 1:
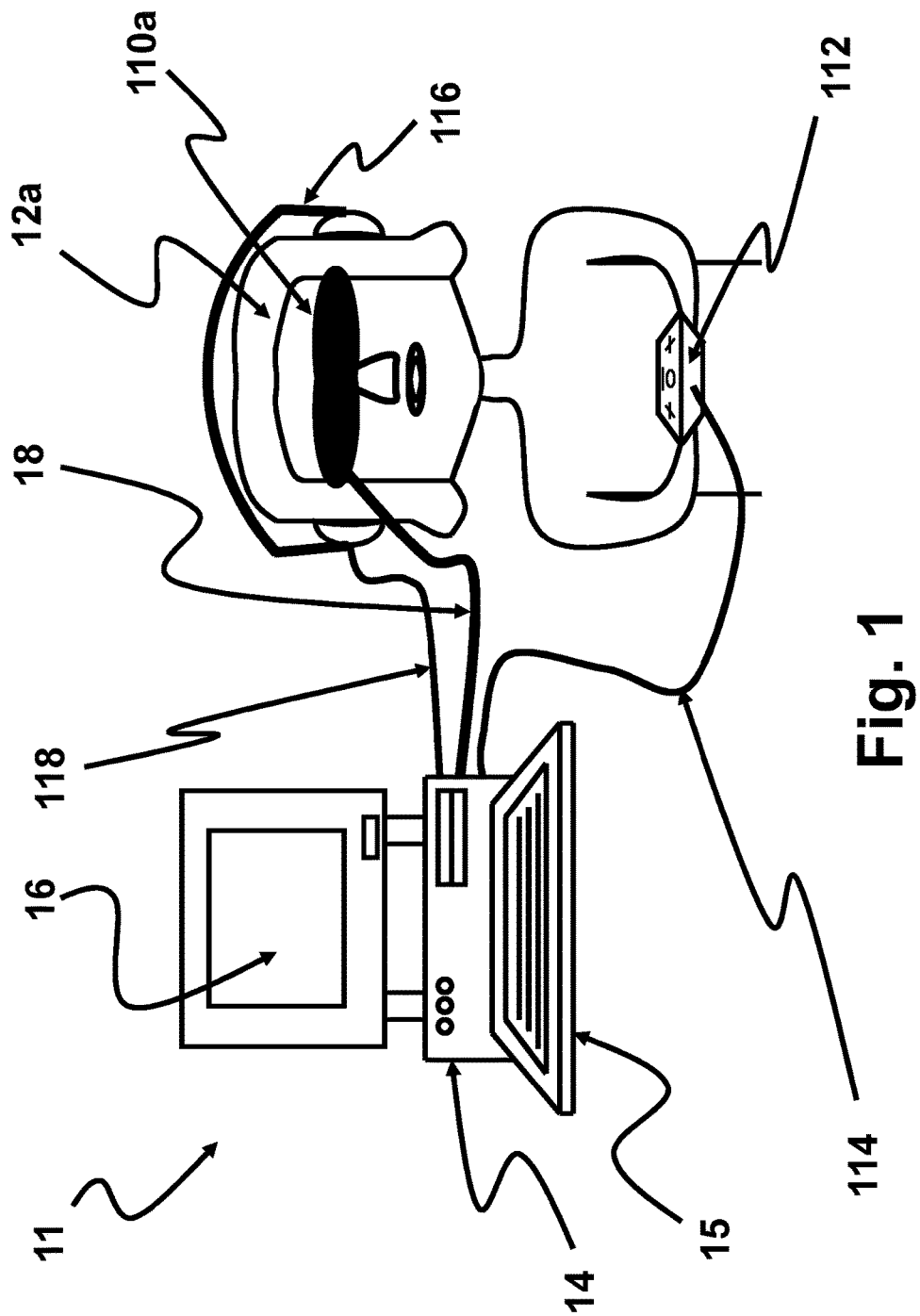
FIG. 1 shows a user undergoing a vision measurement and/or training session involving a computer, a binocular viewer, headphones and a game controller.

In FIG. 1, a human user 12a is shown using a vision measurement and training system 11. Throughout this application, it will be understood that when a vision measurement and training system 11 is referred to, that the system may be used for vision measurement purposes, vision training purposes, or both. The user 12a is shown wearing a binocular viewer 110a connected by an electrical cable 18 to a computer 14, such as a personal computer (PC). The computer 14 is shown fitted with a conventional display 16 that might be a cathode ray tube display, liquid crystal display panel or any other type of conventionally used computer display. As will be clear, the addition of a conventional display 16 is optional. Such a display might be beneficial to allow a care provider or other person to observe the system and possibly better interact with the user 12a. The binocular viewer 110a provides images with varying characteristics suitable for vision measurement and/or vision training purposes. While a separate computer and binocular viewer 110a are shown in FIG. 1, it is possible that electronics miniaturization will allow them to be a single integrated device. A computer other than a PC may be used to control the vision measurement and training system 11. For example, a cell phone, PDA (Personal Digital Assistant), game platform (such as a Playstation® from Sony Corporation, an Xbox® from Microsoft Corporation, or some other game platform), or other computing device capable of generating images, receiving user feedback and storing data could all possibly perform the function of the computer 14 in FIG. 1.

The vision measurement and training system 11 as shown also includes a keyboard 15 and a game controller 112. These devices allow the user 12a or a care provider (care provider is not shown in FIG. 1) the ability to feed signals to the computer 14 that allows the system to assess the vision capability of the user 12a, control ongoing measurement, tracking or training routines and record results. The game controller 112 is shown connected to the computer 14 with an electrical cable 114. Other human input devices besides keyboards and game controllers can also be used to allow the user 12a to feed signals to and control the computer 14. Examples include joysticks, microphones, a mouse, touch pads, foot pedals, steering wheels and all other possible human input devices. Speech recognition or voice recognition devices may be used for human input and could be important for persons who may have difficulty in operating other types of devices (for example, users with coordination problems, arthritis, or other conditions). The addition of human input devices allows the user 12a to react to images and feed signals to the vision measurement and training system 11. This feedback information can be used to allow the system to measure the vision of the user 12a and adapt training to their specific needs. It also allows statistics on the performance of the user 12a to be measured and possibly logged. Simple gaming examples with simple scoring are possible, but very sophisticated information on how rapidly the user 12a can focus, the limits of their focus both in depth and laterally, information on how sensitive and effective various areas of the retina are in sensing light and color, information on how the vision of the user 12a is affected by light intensity and many other useful measurements and statistics can be collected. It is also possible for the system to keep logs on when a given user 12a used the system, for how long and with what results. Clearly, this information could be very useful to a care provider monitoring the vision capability of the user 12a or could be useful in allowing the system to adjust training based on past results.

FIG. 1 also shows headphones 116 connected to the computer 14 by an electrical cable 118, so that audio stimulus may be included. Other options for audio stimulus include speakers on the computer, speakers on the binocular viewer 110a, external speakers, or other methods. Audio can enhance the user 12a experience and benefit vision training by enhancing the concentration of the user 12a on various aspects of a video image. Stereoscopic audio, surround sound, 3D audio effects and the like can all be effectively applied. It should be clear that other stimulations that are common in video gaming systems can also be applied. These include vibration effects through the game controller 112, auxiliary lighting, motion or vibration of the chair (not shown in FIG. 1) of the user 12a and any other possible stimulation of the user 12a. It is noted that while the binocular viewer 110a, headphones 116 and the game controller 112 are shown connected with electrical cables, that other connections including wireless connections for these devices are also possible. If electrical cables are used, it may be possible to combine some of them into shared or combined cable connections.

Figure 2:
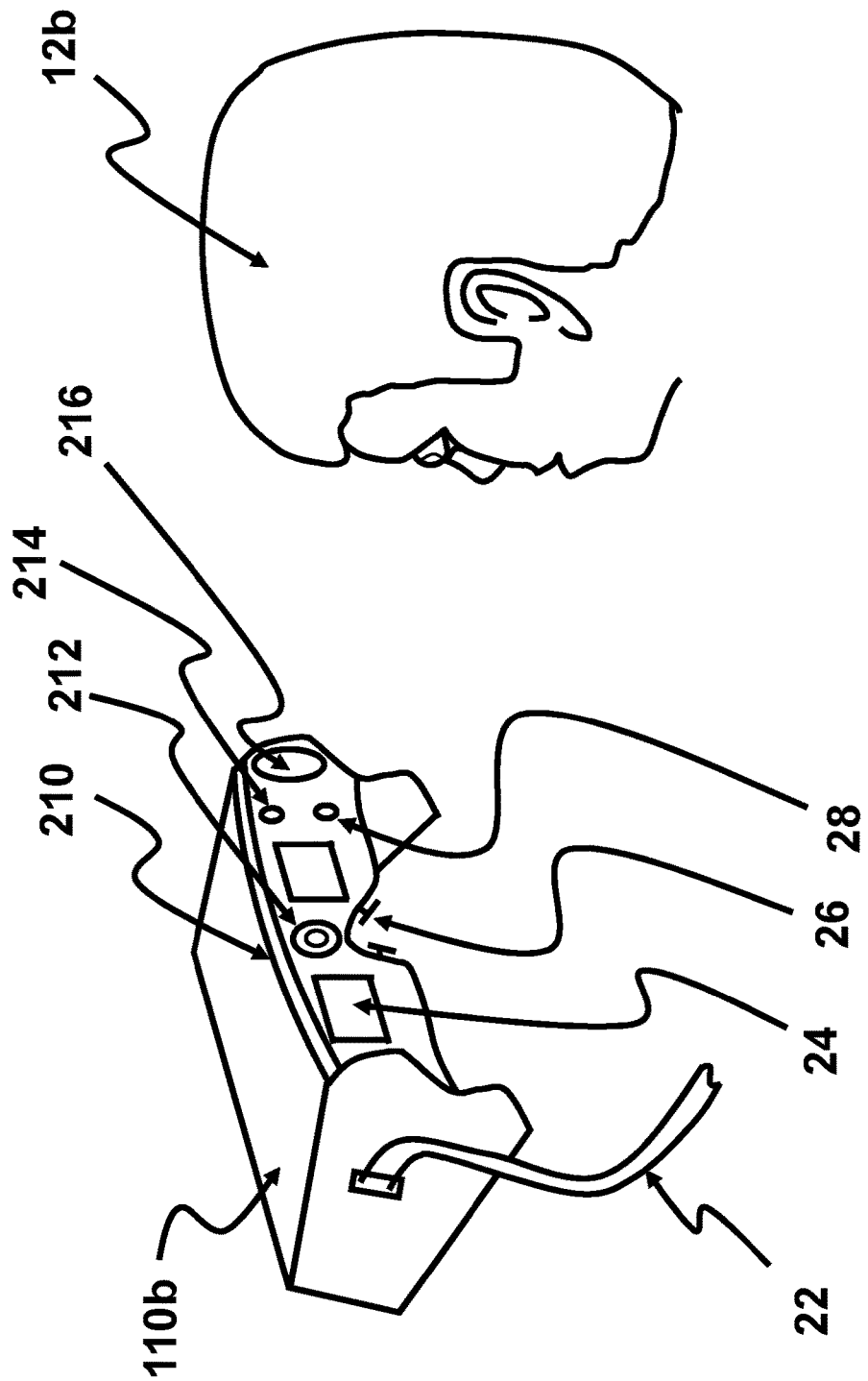
FIG. 2 shows a user and a binocular viewer, the viewing ports, auxiliary features and features to enhance alignment of the binocular viewer to the user's face.

FIG. 2 shows a user 12b and a binocular viewer 110b. Throughout this patent application, the user 12b and the binocular viewer 110b will be considered equivalent to the user 12a and binocular viewer 110a of FIG. 1. The purpose of FIG. 2 is to clarify several detailed aspects of the binocular viewer 110b and how it is fitted to the user 12b, but the operation and use will be within the vision measurement and training system 11 of FIG. 1. Hence, while different in appearance and level of detail shown, the binocular viewer and user of FIG. 1 and FIG. 2 are equivalent. In FIG. 2, the binocular viewer 110b is shown in front of the face of the user 12b. Of course, the user 12b actually wears the binocular viewer 110b in actual use and they are shown apart only so that some details of the viewer can be made visible. The binocular viewer 110b includes a head strap 22 to securely mount the binocular viewer 110b to the head of the user 12b. The head strap 22 is shown only on the left side of the viewer and is not shown as a completed strap to avoid unnecessary clutter in the drawing. Of course, other mounting techniques such as semi-rigid head mounts, harnesses, helmets, or other methods are also possible. Desktop stands, wall mounting or other support systems may also be used. Whatever method is used to mount the binocular viewer 110b, it is important for some vision measurements that the face and eyes of the user 12b be accurately and consistently aligned to the binocular viewer 110b. Special features to enhance accurate and consistent alignment are possible such as the head piece 210, temple pads 216 and nose pieces 26 shown in FIG. 2. These and other possible alignment devices may be fixed or adjustable to enhance fit, comfort and alignment. As will be described later, the vision measurement and training system 11 may include eye tracking or other automatic techniques to determine if the binocular viewer 110b is accurately aligned to the face and eyes of the user 12b and either signal the user 12b to correct misalignment or possibly make electronic adjustments to the collected data to account for small misalignments.

The user 12b in FIG. 2 views images through the viewing ports 24. The viewer may also include auxiliary lights within the viewer such as lights 28 and 214. These auxiliary lights may be used in some vision measurements to draw the eyes of the user 12b to a specific direction or to assess how a user 12b reacts to light stimulus outside the normal field of view of the binocular viewer 110b. While auxiliary lights 28 and 214 are shown in the outside periphery of the binocular viewer 110b, they could be placed anywhere the user 12b can see while wearing the binocular viewer 110b. Another useful feature for vision measurement and training is an eye tracking device. In FIG. 2, binocular viewer 110b includes an optional video camera with lens 212. This video camera may be used to monitor the eyes of the user 12b so that eye tracking software and hardware either within the binocular viewer 110b or within the computer 14 shown in FIG. 1 may provide the vision measurement and training system 11 with information regarding the direction that the user 12b is looking at any given time. Eye tracking devices and technology are well established and the details of their operation will not be described here. Some binocular viewers 110b may include additional auxiliary displays in the peripheral regions of the viewer to extend the ability to provide visual stimulus beyond the viewing ports 24. Other features inside the binocular viewer 110b might include a vibrator to massage the area around the eyes of the user 12b, a heater to warm and sooth the eyes of the user 12b, a humidifier to keep the eyes of the user 12b moist, or other possible features to enhance comfort or contribute to vision measurement or training. And additionally, some binocular viewers 110b may include gyroscopes, accelerometers, or other motion sensing devices so that movement of the head of the user 12b can be sensed and accounted for.

In addition to the binocular viewer 110b shown in FIG. 2, other methods of generating images suitable for measurement and training are also possible. However, alignment to the eyes of the user 12b should be accounted for if measurements related to vision acuity in particular areas of the visual field are to be performed. This alignment can be accounted for mechanically as illustrated in FIG. 2 or as noted, by eye tracking as with camera with lens 212 in FIG. 2 or through electronic analysis and correction of the data as will be described later. Also, it is essential for some vision measurements that each of the eyes of the user 12b be assessed separately. Hence, other methods suitable for generating images for vision measurement and training include glasses with light shutters synchronized with a display (this is cumbersome and requires large shutters for the display that are not conventionally available), use of polarized light and polarized lenses to separate views for each eye (requires a polarized display that is not conventionally available), use of light of different colors and colored filter eye glasses (this constrains the ability to measure sensitivity to color), holographic display technology (expensive and laser light makes it very difficult to measure focusing ability), or other methods. Each of these methods has some serious drawbacks as noted and all of them suffer from lack of an ability to easily and consistently adjust focal depth as will be explained later for the binocular viewer 110b. It is also possible to provide a system without binocular capability, however this would substantially detract from the breadth of possible measurements and vision training that could be offered.

Figure 3A:
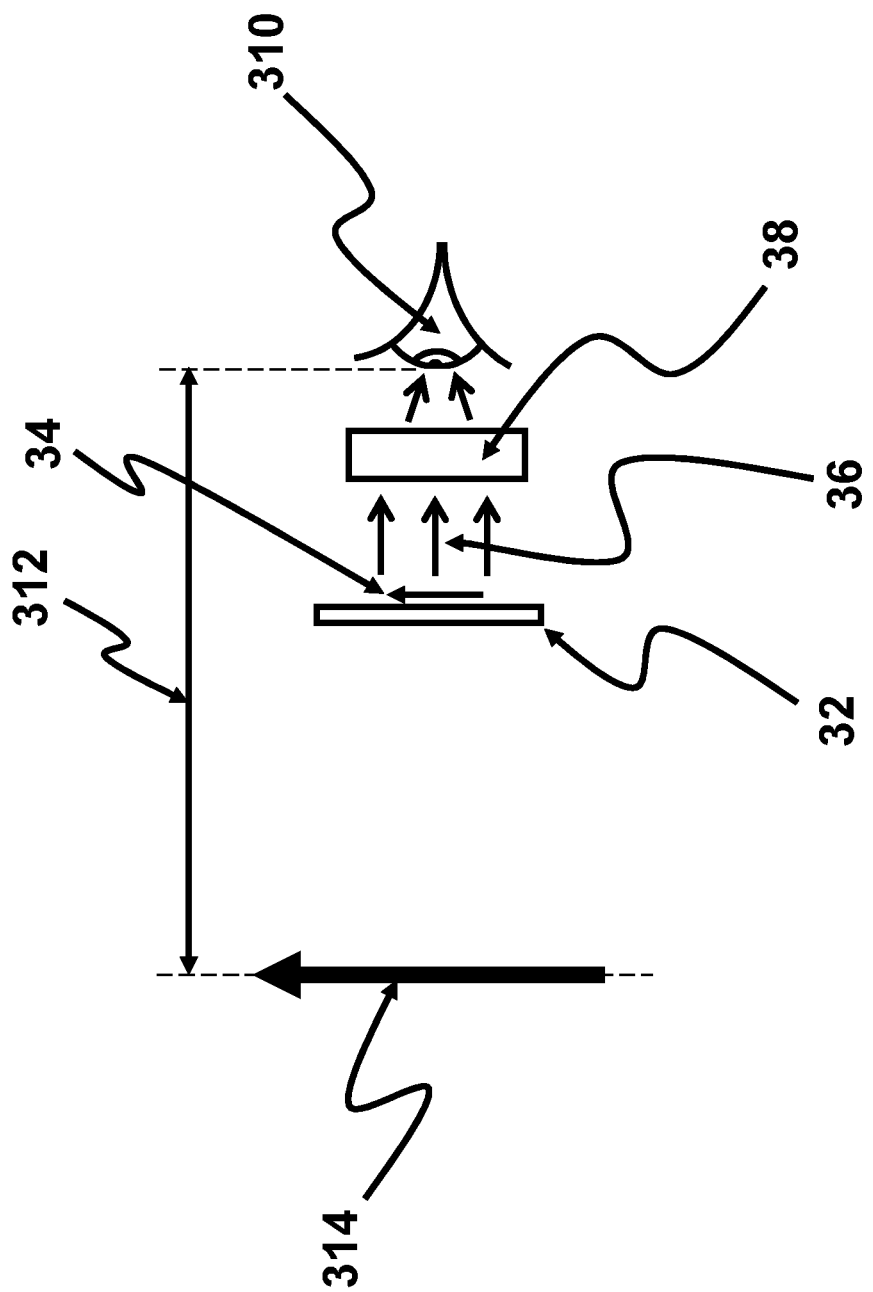
FIG. 3A shows a side view of a user's eye and the elements of a display system that is capable of projecting a virtual image such that the image appears at a different distance, the focal depth, instead of the actual distance from the user's eye to the actual display screen.
Figure 3B:
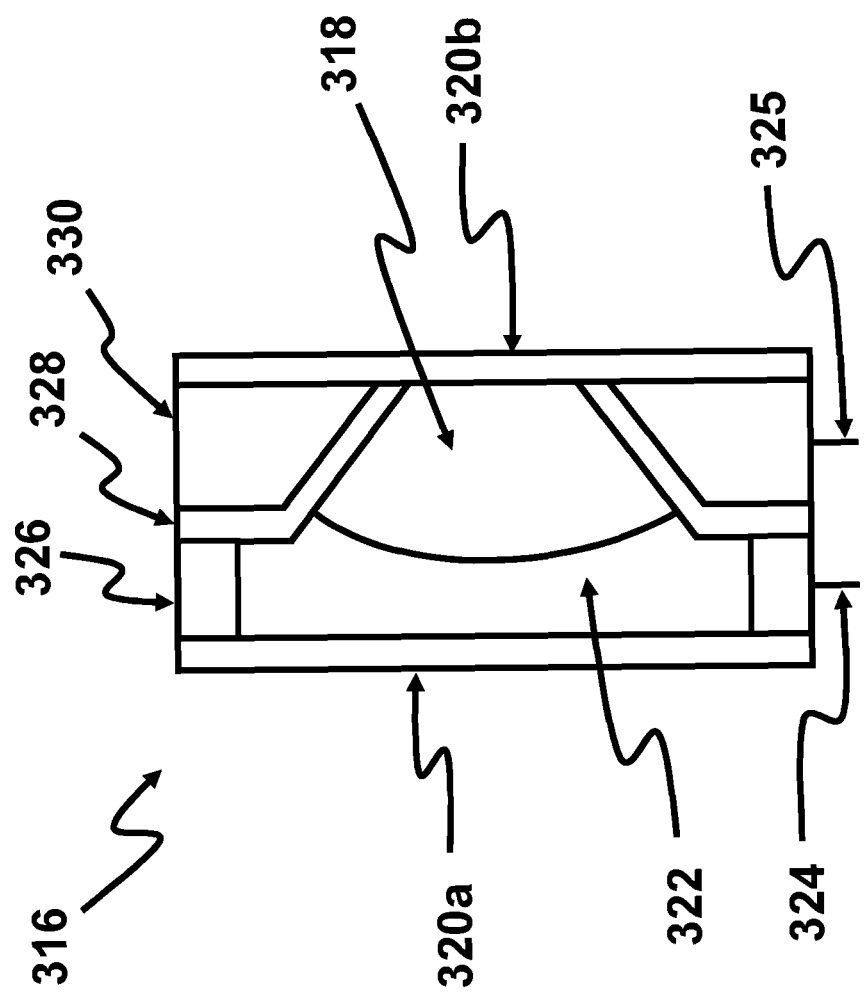
FIG. 3B shows a cross-sectional view of a fluid lens that could be used to implement an optical subsystem.
Figure 4:
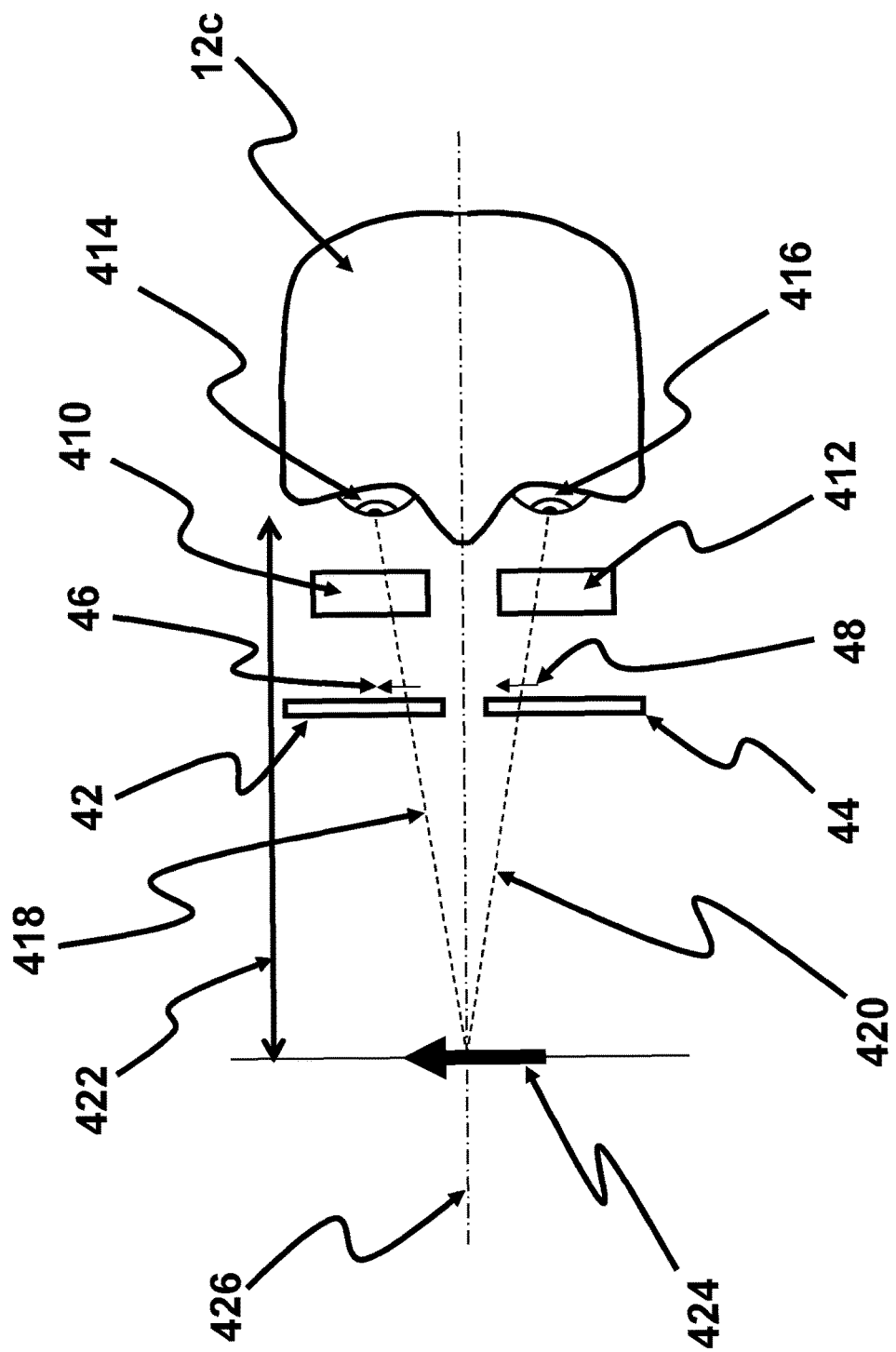
FIG. 4 shows a top view of a binocular version of the display system shown in FIG. 3A illustrating, in particular, the effect that parallax may have on how a user perceives the distance to an object.

FIG. 3A, FIG. 3B and FIG. 4 show part of the internal construction of the binocular viewer 110a and 110b shown in FIG. 1 and FIG. 2, respectively. As noted previously, these are equivalent, so for simplicity, this application will normally refer to them only as binocular viewer 110b. FIG. 3A shows a side view of a human eye 310 and the elements of a monocular display system. In this preferred embodiment, the monocular display system shown in FIG. 3A would be incorporated into each side of the binocular viewer 110b that is shown in FIG. 2. In FIG. 3A, a display element 32 generates an image 34 that passes through an optical subsystem 38 and then passes on to the human eye 310. Light rays 36 are included in FIG. 3A for illustrative purposes. The image 34 is shown in FIG. 3A slightly in front of display element 32 since the FIG. 3A is a side view and it cannot be illustrated otherwise. Of course, in a real system, the image 34 would be projected from the surface of the display element 32 that is facing the human eye 310. The display element 32 is a liquid crystal display (LCD) in this preferred embodiment. However, other display technologies such as plasma displays, OLED (Organic Light Emitting Diode), cathode ray tubes, laser display systems, MEMS (Micro Electro Mechanical System), and many other display technologies could also be used. Additionally, the display element 32 might not consist of a single element, but might also include mirrors, lens, optical fiber, lasers, or other optical devices that allow an image to be created in some other location and the image display to be projected in a manner to achieve the same effect for the user 12b as shown in FIG. 3A. The optical subsystem 38 processes the image 34 so that the human eye 310 will see the virtual image 314 in focus seeming to appear at a distance equal to the focal depth 312. Of course, the virtual image 314 is the only representation of the image 34 that the human eye 310 actually perceives. The optical subsystem 38 might be formed with mirrors, prisms, lens, optical sensors, digital optical processors, fluid lenses, moving mirrors, moving lenses, MEMS structures, deformable lenses, micro mirrors or other elements. The optical subsystem 38 is responsive to electronic control so that the effective focal depth 312 that the virtual image 314 appears at can be varied by control either from the binocular viewer 110b or the computer 14. It is also possible with certain constructions of the optical subsystem 38 that focal depth of the optical subsystem 38 can be varied as a function of circumferential location so that astigmatism can be generated or compensated. Astigmatism can also possibly be addressed by monitoring the effect of different focal depths to the user 12b as a function of location within the field of view of the user 12b.

In FIG. 3B, a cross-sectional view of an embodiment of optical subsystem 38 consisting of a fluid lens 316 is shown. As noted above many other embodiments of the optical subsystem 38 are possible. In FIG. 3B, transparent windows 320a and 320b contain two fluids which have been selected so that they don't normally mix with each other. The first fluid 322 is normally a conductor such as water containing ions and the second fluid 318 is normally an insulator such as oil. First electrode 326 contacts the first fluid 322 and insulator 328 separates second electrode 330 from the fluids. As the potential voltage across first electrode contact 324 and second electrode contact 325 is varied, the potential from first electrode 326 and second electrode 330 varies. Since first electrode 326 is in contact with first fluid 322, the potential between first fluid 322 and second electrode 330 is also varied so that the electrostatic potential between them alters the shape of the interface between first fluid 322 and second fluid 318. In this way, the focal length of fluid lens 316 is responsive and variable based on the potential voltage applied across first electrode contact 324 and second electrode contact 325. Refraction of light entering transparent window 320a from the left of FIG. 3B passing through fluid lens 316 and exiting transparent window 320b will be refracted by fluid lens 316 by an amount that is variable based on the potential voltage across first electrode contact 324 and second electrode contact 325. Clearly, fluid lens 316 if applied in FIG. 3A will provide the necessary function of providing a variable focal length optical function that is responsive to electronic control.

Throughout this patent application, the term adaptive focal depth shall mean the ability to control the focal depth 312 electronically. This term is used regardless of the specific construction of the binocular viewer 110b and whether the control is from the computer 14 or is generated internally within the binocular viewer 110b itself. As will be explained later, adaptive focal depth may be used in the vision measurement and training system 11 to automatically compensate for refractive disorders, adjusting the focal depth 312 to correspond to other aspects of an object that contribute to the distance at which the user 12b perceives it, or to intentionally keep an object out of focus for a specific purpose. Adaptive focal depth may be used by the user 12b to control the focal depth 312 manually through the game controller 112 or other human input device connected to the vision measurement and training system 11. Adaptive focal depth may also be used by the vision measurement and control system 11 to automatically create desired combinations of focal depth, parallax and perspective in an image.

In this preferred embodiment the optical subsystem 38 provides capability to allow the focal depth 312 to be varied. However, for some vision measurements and training, a fixed focal depth 312 is acceptable. For example, when dealing with eye diseases that primarily impact the retina (for example, macular degeneration) it may not be important to vary the focal depth 312. In such a case, a display with a fixed focal depth 312 could be used. However, even in such cases where variable focal depth 312 is not strictly essential, it can still be beneficial to vary the focal depth 312 to account for any focusing disorder the user 12b may suffer. That is, the vision measurement and training system 11 can account for the need for minor adjustments to the focusing ability of the user 12b (for example, nearsightedness) so that very sharp and clear images result leading to more accurate vision measurements. It may also be beneficial to vary the focal depth 312 to exercise and relax the eye's 310 focusing mechanism so that possible eye strain related to viewing at a constant focal depth may be reduced.

It is noted that as the optical subsystem 38 is used to change the focal depth 312 of the image, that some variation in the perceived size of the image may occur. Whether this is a problem depends on how the optical subsystem 38 is constructed and on the type of vision measurement or training being undertaken. However, since the display element 32 is under computer control, it is possible to simply adjust the size of the image as generated on the display element 32 to counter act any change in the size of the virtual image 314 as the focal depth 312 is varied. Clearly, this adjustment to image size is optional and whether or not it is included is a function of the desired images to be generated.

In FIG. 4, a top view shows some details of the internal construction of binocular viewer 110b. As discussed above with regard to FIG. 3A, the binocular viewer 110b of FIG. 2 includes the monocular system that is illustrated in FIG. 3A in front of each eye of the user 12b, and this construction is further illustrated in FIG. 4. The left eye 416 of a user 12c views the image pictured on the left display element 48 as the virtual image of the binocular display system 424. The image pictured on the left display element 48 is produced on the left display element 44 and is processed by the left optical subsystem 412. Similarly, the right eye 414 of the user 12c views the image pictured on the right display element 46 as the virtual image of the binocular display system 424. And, the image pictured on the right display element 46 is produced on the right display element 42 and is processed by the right optical subsystem 410. The virtual image of the binocular display system 424 appears to the user 12c at the focal depth of the binocular display system 422. As noted above with regard to the monocular system of FIG. 3A, the focal depth of the binocular display system 422 is variable under automatic control in this preferred embodiment through control of the right and left optical subsystems 410 and 412, but it is also possible to provide a system beneficial for some measurements or training that uses a fixed focal depth.

As noted above, the right and left optical subsystems 410 and 412, process the image so that the virtual image of the binocular subsystem 424 appears in focus at a distance equal to the focal depth of the binocular display system 422. Additionally, in the binocular display system shown in FIG. 4, the angle that the images are viewed at for each eye also contributes to the perception of distance that the user 12c experiences. In this preferred embodiment, the angle between the left line of sight 420 and the right line of sight 418 will be adjusted to correspond to the focal depth of the binocular subsystem 422 so that the user will not see multiple images, a single image out of focus, or other impairments, but rather, will see the virtual image of the binocular display system 424 in focus and correctly. The angle of the lines of sight of a user's eyes to a viewed image is commonly referred to as parallax and this term will be used herein. The position of the image pictured on the left display element 48 and the image pictured on the right display element 46 can be adjusted to be closer or further from the binocular display system virtual center line 426 so that the angle between the left line of sight 420 and the right line of sight 418 will correspond to the focal depth 422 and the user 12c will perceive the focal depth and parallax of the image to be consistent. It is noted that since the distance between each individual user's eyes is different, this information may need to be determined by a calibration routine or otherwise it could simply be entered into the system. Clearly, for parallax and focal depth to be properly coordinated, the distance between the eyes of the user 12c should be accounted for. In a three-dimensional (3D) binocular viewer such as the one illustrated in FIG. 4, the images provided to each of the eyes of the user 12c is slightly different as the user will see the virtual image from a different perspective from each eye. This is a very common technique known as stereoscopic vision and it will be used in some of the measurement and training techniques herein. It is noted that unlike the drawing in FIG. 4 that shows the image pictured on the left display element 48 and the image pictured on the right display element 46 as identical images. If stereoscopic vision is used, these images should be slightly different to account for the different perspective view each eye would see if a real object were present at the location where the virtual image of the binocular display system 424 is perceived to be. In this way, a binocular viewer 110b allows the user to see a seemingly real 3D image if stereoscopic vision is used.

In addition to parallax and focal depth as described above, other aspects of human vision also affect the distance a person perceives to a given object. Perspective, for example, is the way one views closer objects to be larger, more distant objects to be smaller, and parallel lines in an image to converge at a vanishing point in the distance. Of course, perspective is very well known and won't be discussed in detail here. Another aspect of how far one perceives things to be away is called motion parallax. Motion parallax is the effect that objects close to us appear to move past us faster than do more distant objects. Other aspects such as lighting, shadowing, absolute size of familiar objects, and other effects also play a role. Hence, there are many aspects to making an image appear to have true depth. For the purpose of simplicity herein, parallax will only be referred to specifically with regard to FIG. 4, perspective and focal depth. It is understood that other known additional techniques may be applied and may be necessary to create a fully realistic image as would be beneficial for some of the techniques described.

The vision measurement and training system 11 including binocular viewer 110b with adaptive focal depth, that is with the internal construction shown in FIG. 4, is capable of measuring or training the eyes of the user 12b in multiple ways. The parallax and focal depth of the virtual image can be made consistent so that the user 12b sees a very real 3D image that includes the depth and perspective a real object would if similarly viewed. Focal depth 312 can be adjusted separately for each of the eyes of the user 12b so that symmetry problems with vision can be addressed. The vision measurement and training system 11 of FIG. 1 is capable to measure or train the eyes of the user 12b in a very complex and sophisticated manner. Visual field, refractive errors, astigmatism, retinal disorders, double vision, and many other vision measurements can be performed, and, where appropriate, vision training may also be undertaken. For example, the binocular system as described can vary focal depth for each eye and parallax separately so that diplopia (double vision) caused by a refractive disorder can be compensated so that binocular vision is reestablished, allowing other measurements or training to be undertaken. Moving images laterally in the same manner that prism therapy is used for treating strabismus is also possible. Very many measurements and training regimens are possible.

Another benefit of the binocular viewer 110b with adaptive focal depth is that since the perspective, parallax and focal depth of an object of interest within an image can all be consistent with each other, the user 12b will not normally sense something unnatural about the images he/she is viewing. This is potentially very important as an issue with conventional binocular viewers is that users 12b sometimes experience headaches, dizziness, or other discomforts when using them. As the binocular viewer 110b with adaptive focal depth provides more natural images, it is possible that some users 12b will experience less discomfort when such a viewer is used. This benefit is similar to the well known situation that a person with an incorrect eyeglasses prescription may suffer headaches, dizziness and other possible discomforts. By ensuring correct accommodation for the image being shown, enhanced user 12b comfort is clearly possible.

In spite of the sophistication of the binocular viewer 110b, it is still not capable to provide a perfectly realistic view of a real world image. Herein, an image is the complete scene a user 12b sees through binocular viewer 110b and to objects within the image as individual features, items or elements within the image. For example, a view down a street is an image, but each car parked along the street is an object. In the real world, of course, all objects within an image are not at the same distance. Consequently, each object in an image has different parallax depending on its distance from the person viewing it and the angle it is viewed at. And, of course, the focal depth is different for each object in an image depending on its distance from the person viewing it. It is possible that the optical subsystem 38 as shown in FIG. 3A could be eventually so sophisticated as to make each object in a full image to have a different focal depth 312 so that the eye would have to adjust its focus for each object just as it does in the real world. If this capability were available, it would then only be needed to alter the position of the objects in the images in the two display elements shown in FIG. 4 so that the parallax of each object was also correct and a near perfect, real-world, image could be created.

However, since the vision measurement and training system 11 is based on properly viewing objects at different distances, locations and orientations, it is important that the object of particular interest in an image have the desired parallax, perspective and focal depth. This effect can be achieved by making the object of interest capture the attention of the user 12b so that other objects in the image that will invariably have different levels of error in their parallax and/or focal depth are not so noticeable. For example, in a video game where the user 12b is shooting virtual bullets at an enemy plane, the enemy plane is the object of primary interest to the user 12b. If the parallax and focal depth are correct for the user 12b, the eyes of the user 12b will alter their focus as the enemy plane moves in the field of view and moves to varying distances. The enemy plane in such a case might be shown in bright colors and with crisply defined features. In contrast, the background scenery, sky, landscape, and other objects in the display might be portrayed in duller colors and might be intentionally blurred to make them less interesting to the user 12b. In this way, the vision measurement and training system 11 can achieve its goal to measure and train the eyes of the user 12b without requiring a perfect display system, but rather with the practical binocular viewer 110b including the internal construction shown in FIG. 4 that can be produced with existing technology.

Figure 5:
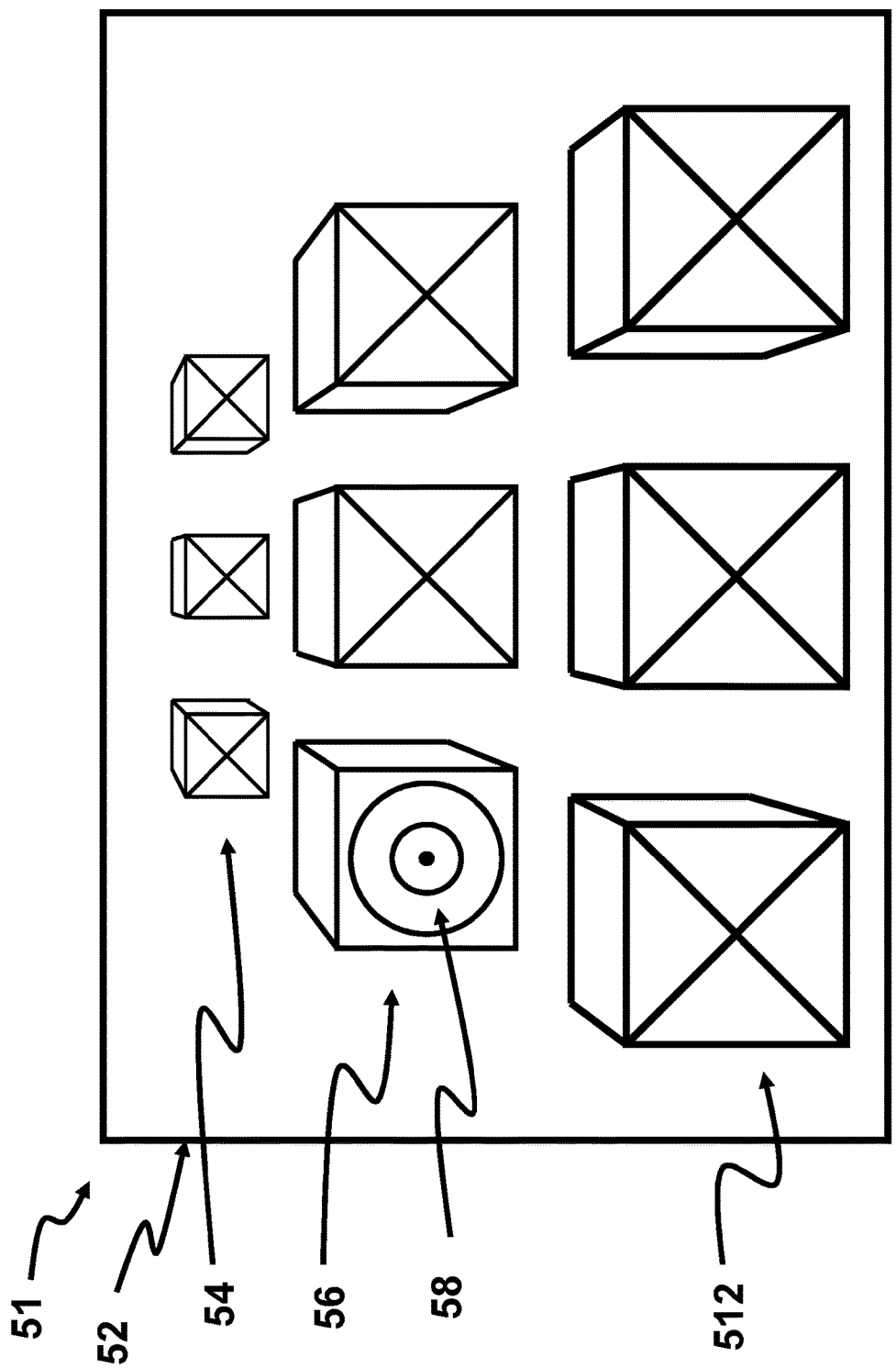
FIG. 5 shows an image that could be used to measure or train a user's vision acuity at different focal depths.

Now that the construction of the binocular viewer 12b is understood, it is possible to explain how vision measurements can actually take place. In FIG. 5, a video display image 51 is shown that could be used for this purpose when viewed through binocular viewer 110b. Within the display screen boundary 52 in FIG. 5, there are nine box images. Each box except one has a cross on its front surface that extends diagonally from corner to corner. The upper row of box images 54 includes three boxes that appear at the furthest distance from the user 12b. The middle row of box images 56 includes three boxes appearing at a medium distance. And the lower row of box images 512 includes three boxes that appear closest to the user. It is noted that through a binocular viewer 12b, the image of FIG. 5 would appear to have real depth as a true stereoscopic vision image would be provided. As patent applications are limited to flat drawing sheets, the perspective drawing in FIG. 5 is the best that can be provided. It should be clear that in a real system, again using a binocular viewer 110b, the parallax and perspective of each box in FIG. 5 would be correct so that a very realistic image would be visible. A target 58 is shown on the left most box in the middle row of box images 56. In the measurement used with the image of FIG. 5, the various boxes are highlighted and a target 58 appears on each of them randomly over time. Only one box has a target 58 on it at a time, all the others have crosses. The strategy for the measurement is for the user 12b to quickly point a cursor or crosshair on the target and detect the image with whatever human input device is available as rapidly as possible. The system then logs the delay and the accuracy with which the user 12b completed this task and determines a performance score. As the target is moved from one row to another, the focal depth of the binocular viewer 110b is altered to correspond to the perspective and parallax of the boxes in that row. In this way, the ability of the user 12b to focus at varying distances can be assessed. Over the course of many such measurement sequences, the system can develop a composite score for the user 12b and can assess the ability of the user 12b to play the game. Range of focus, time to focus, refractive correction needed, and time to assess a target are only some of the many measurements that can be recorded.

The target 58 shown in FIG. 5 is a simple circular target for simplicities sake, but it is clear that a more sophisticated target could be used. For example, the capital letter E is sometimes used for vision focusing assessment in which the person under test is asked by an optometrist to state which direction the letter is rotated (the normally horizontal elements of the capital E that normally point to the right may point up, down, or to the left or right) to determine the person's ability to focus at a given distance and text size. By replacing the simple circular target 58 in FIG. 5 with a capital E scaled to various sizes and at different distances depending on which row of boxes it appears and asking the user 12*b* to signal the orientation of the letter each time it appears, the simple game described above in FIG. 5 is clearly extended to be very similar to a professional vision assessment from an optometrist. Of course, it is also possible to direct a user 12*b* to view a particular object and simply adjust the focus, through the game controller 112 or other human input device used in the vision measurement and control system 11, much as one would with a pair of binoculars and then simply record the focal depth settings to assess the vision of the user 12*b*.

It is noted that in a gaming feedback system such as the vision measurement and training system 11 described herein, that reaction time and errors made by the user 12*b* should be accounted for. Clearly, the time taken for the user 12*b* to acknowledge a target 58 in the game explained with regard to FIG. 5 includes not only the time needed to focus on and recognize the target, but also on the human reaction time to acknowledge the target 58 via the human input device. However, the system can easily measure reaction time by engaging the user 12*b* to watch a single box and simply acknowledge the target 58 each time it blinks or changes size, shape, etc. In this way, reaction time apart from focusing time or ability can be assessed. It is also clear that the user 12*b* will occasionally make an error and acknowledge a target 58 before it has been fully recognized or possibly be distracted and delay an acknowledgement. However, since the system would take many dozens or even hundreds of measurements to assess vision performance, it is possible to generate statistics, determine a standard deviation of the time to acknowledge a target 58 as a function of range and location and simply eliminate any deviant or erroneous measures from the database.

The vision measurement and training system 11 can also use the image of FIG. 5 for vision training. Through the measurement sequence described above, the vision acuity of the user 12*b* as a function of distance can be assessed so that the level of accommodation (strength of external lenses the user requires to see clearly and in focus) the user requires for each row of boxes is known. With this information, many possible training regimens are possible. For example, the vision measurement and training system 11 may provide the user 12*b* with slightly less accommodation (in an absolute sense) than is normally required for each row of boxes so that the user 12*b* is forced to use their own eye's focusing ability. In this way, the user 12*b* is forced to struggle somewhat to focus at all ranges and trains his or her eyes to focus at their limit. It is important that for such a training regimen that the user 12*b* only be requested to struggle mildly to focus as, if too much is demanded, the user 12*b* will simply not be able to see adequately and may give up the game. The appropriate level of focus to demand of the user 12*b* can clearly be determined by altering it over some range and noting the user 12*b* responses and ability to play the game. Hence, the ability to continuously assess the focusing ability of the user 12*b* and to pace the progress of the training to his or her present ability is a key important aspect that is only possible with a mechanism for adaptive focal depth 312 as described above. The system for adaptive focal depth is also beneficial in that it can allow the user to be forced to struggle somewhat at all ranges. In this way, the user is constantly (albeit mildly) challenged so that the training may be more effective. It is also noted that this ability to force the user 12*b* to struggle to focus could be limited to one eye. If only one eye is to be trained in this way, the image in front of the other eye may carry only a vestige of the target image to help the user 12*b* maintain a sense of perspective and parallax, while forcing the eye being trained to bear the burden of accurate focusing. It is also possible to show a partial view of the video display image 51 of FIG. 5 to the eye not being trained and a complete image to the eye being trained. For example, the eye not being trained might be offered the video display image 51 of the boxes without either the target 58 or the crosses on their front faces. The eye being trained would receive the full image with the targets 58 and crosses so that the full training burden would fall to that eye. In this way, the eye not being trained would see enough of the video display image 51 that the user would maintain a comfortable sense of parallax and perspective while not in any way helping the user 12*b* in responding to the stimulus of the target 58.

Figure 6:
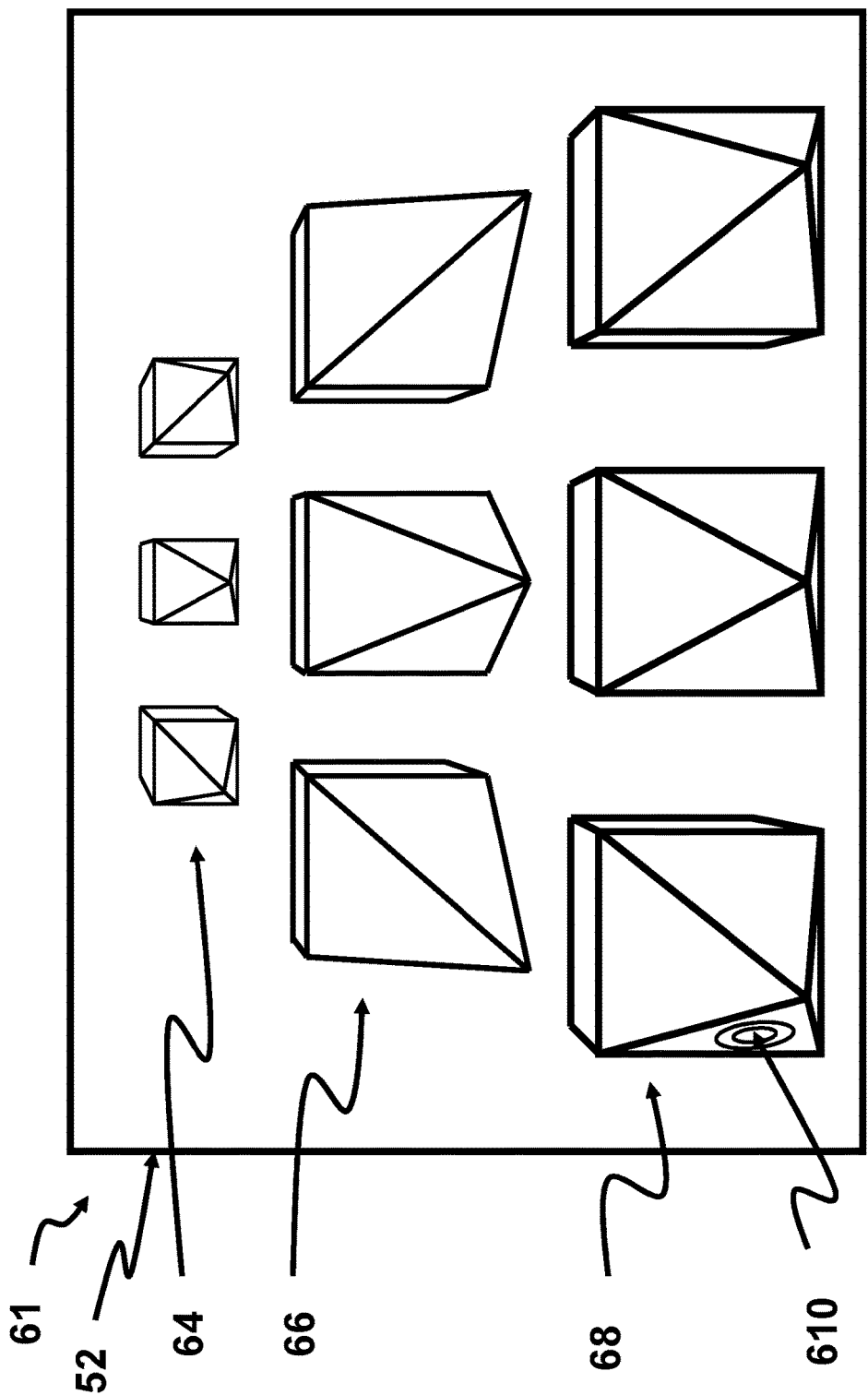
FIG. 6 shows an image that could be used to measure or train a user's vision acuity in each eye separately while the user is viewing the image with both eyes at the same time.

This scheme can be taken further with a video display image of pointed objects 61 as shown in FIG. 6. In FIG. 6, within the display screen boundary 52, pointed objects are displayed with the binocular viewer 110*b* and are positioned and oriented so that only one of the eyes of the user 12*b* sees some of the surfaces of the pointed objects. This is illustrated in the lower row of pointed objects 68 where a target on a side of a pointed object 610 is shown on the left side of the left most pointed object. While it is, again, not possible to fully portray the nature of the 3D stereoscopic vision image on a flat drawing sheet, it is clear that the image could be configured so that the target on a side of a pointed object 610 would only be visible in the left eye of the user 12*b*. This is illustrated, to the degree possible, with the middle row of pointed objects where longer points have been used so that as drawn in perspective, some sides of the pointed object cannot be seen. Of course, with a binocular viewer 110*b*, some portion of the otherwise not visible parts of the objects would become visible to one of the eyes of the user 12*b*. FIG. 6 also includes an upper row of pointed objects 64 to better show how the overall image includes objects at various distances. Using the video display image of pointed objects 61, and the game sequences described above with regard to FIG. 5, it is clear that the user 12*b* would unwittingly provide information through his or her game play regarding the vision of only one of his or her eyes at a time due to the clever location of objects in the 3D image where only one eye can actually see them. This capability is particularly important for users 12*b* that have asymmetry in their vision (one eye has substantially different vision ability than the other), convergence problems, or difficulty with fusing (combining) the view from each of their eyes into a single neural image. Clearly, the technique of FIG. 6 is quite beneficial in such cases as the user 12*b* views a single and very natural image while each eye can be measured separately.

Of course, many additional aspects of vision acuity can also be measured with the vision measurement and training system 11 described herein. While the system could be implemented in monochrome, the use of polychrome (i.e. color) displays allow the system to assess visual acuity as a function of color. By changing the rate at which an image changes, the ability of the user 12b to focus rapidly could be measured. With more sophisticated images, the ability of the user 12b to maintain focus as an image moves laterally or closer or further from the user 12b could be assessed. Vision acuity as a function of motion, color, brightness, focus, speed, location on the retina, contrast and many other possible aspects can be measured and appropriate training regimens can be developed. Even aspects of vision that require a distortion in the image or optics of the binocular viewer, such as astigmatism, may be measured.

It is noted that the video images, shown in FIG. 5 and FIG. 6 are very simple examples used to illustrate how the system can assess and train the vision of the user 12b. Clearly, much more complex, changing and interesting images and all possible ranges (distances to the objects) can be used. The simple boxes and pointed objects of FIG. 5 and FIG. 6 can be replaced with much more interesting shapes. Animals, flowers and other interesting objects can be included to create very interesting imagery that would appeal to whatever age group the given system is intended for. In this way, a system that provides images much more like those found in nature or in a modern video gaming system can provide the same results while offering the user 12b a much higher level of enjoyment. Of course, the system can also use other information to more rapidly and accurately assess the vision capability of the user 12b. This information can include the vision information of the user 12b that was determined on prior occasions that the user 12b made use of the system, and that information can be automatically logged and stored in the computer 14 for such future use. Other information could be information that the user 12 or a care provider might enter into the system regarding specific aspects of the measurements or training that the care provider wants to control or influence. In some cases, the care provider might want to maintain complete control of the vision measurement and training system 11 and operate the system manually while verbally questioning the user 12b, much as an optometrist works with a patient today.

Figure 7:
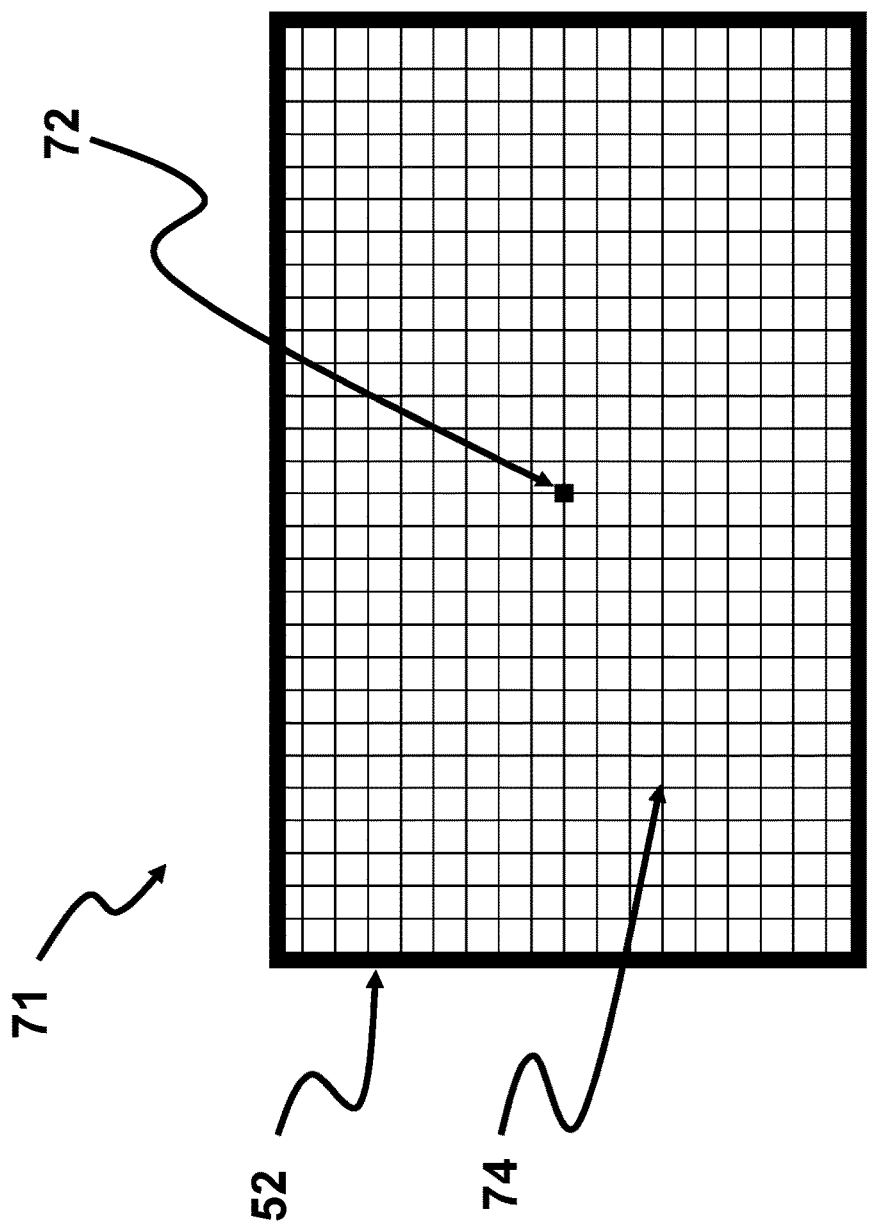
FIG. 7 shows an Amsler grid.

While useful for many vision conditions, FIG. 5 and FIG. 6 dealt primarily with vision measurement and training with respect to focusing disorders. However, a very important class of vision disorders relates to retinal function. Macular degeneration, diabetic retinopathy, glaucoma and other retinal disorders are vision disorders that may be assessed by how well a patient can see throughout their visual field. Measurement, tracking and training are all very important for this class of vision disorders and the vision measurement and training system 11 provides novel ability to provide these benefits. In FIG. 7, the well known Amsler grid 71 is presented. The display screen boundary 52 represents the edge of the field of view of the binocular viewer 110b in this preferred embodiment. The grid lines 74 form grid segments in the crossing vertical and horizontal square grid pattern (square grids are normally used, but rectangular, triangular and other grids are also possible). The center square 72 is also clearly shown. The Amsler grid 71 is widely used as a simple diagnosis mechanism for macular degeneration and other retinal disorders. Normally, a paper grid is used and the patient simply covers one eye and looks at the center square 72. While looking at the center square 72, the patient is asked to observe if any of the segments of the grid are missing, wavy or otherwise distorted. If they are, macular degeneration or other disorders may be present. Patients with macular degeneration are normally asked to do the Amsler grid test very regularly, often daily, and to report any changes in their condition to their doctor. As macular degeneration is a degenerative disorder and certain possible conditions can lead rapidly to blindness if not treated, it is critically important to monitor for changes in a patient's condition.

In this preferred embodiment, the screening capability of a simple paper Amsler grid 71 is extended to provide a more complete measurement, tracking and training capability. Instead of a paper grid, the image of FIG. 7 is a computer display of an Amsler grid 71 shown in the binocular viewer 110b. Looking through the binocular viewer 110b, the user 12b can be tested separately in each eye. The user 12b can use a mouse, game controller 112 or other human input device to indicate where he or she notices missing grid segments, wavy lines, or other distortions. This may be done easily by positioning a cursor on the Amsler grid 71 over the affected area and detecting, but could also be done using reference marks on the display and entering the location manually with a keyboard 15 or other human input device. By simply indicating which regions of the display are affected, the user 12b can quickly input a rough indication of their condition. If each affected Amsler grid 71 segment is indicated (again, either by detecting with a cursor, entering reference numbers or codes, or some other method), a more precise assessment of the condition of the user 12b can be made. The test can be quickly and easily repeated several times to ensure consistent results. Variations in the test are also possible. For example, instead of running the test with black lines on a white background as shown in FIG. 7, the scheme can be reversed so that a white grid appears on a black background. A colored grid with either a black, white or colored background can also be used. Variations in the size of the grid sections and the thickness of the grid lines 74 can be used. Color, brightness, contrast, grid size, grid line 74 thickness or any other possible aspect of the Amsler grid 71 can be varied to provide an enhanced test for macular degeneration or other retinal disorders in each eye. Using a binocular viewer 110b, it is possible to not only test each eye separately, but also to show a combined image to the user 12b so that the ability of the user 12b to compensate for limited vision in one eye with help from the other eye can be assessed. While this is most readily achieved by simply asking the user 12b to indicate any missing, wavy, or distorted segments in the Amsler grid when viewed with both eyes at the same time and to then compare the results to the responses of the user 12b for each eye alone, more sophisticated diagnosis is also possible. One example is to present the Amsler grid 71 to both eyes and then to drop some segments of the grid (or reduce their line width, make them dimmer, etc.) from the view of one eye in an area of that eye that is suspected to be affected by macular degeneration. The user is asked to note if any difference in his or her vision was noticed when the grid segment was dropped or altered. If the user 12b doesn't notice the change, the same segment can then be dropped or altered from the view of the other eye, while maintaining the dropped or altered view for the first eye. When the grid segment is dropped or altered in the view of the second eye, the user 12b should then notice it. In this way, retinal function can be mapped for both eyes while the user 12b views the Amsler grid 71 with both eyes. Such a test verifies the disease-affected area by ensuring that the user 12b does not notice certain changes to the grid through the area of the eye affected by disease. In this way, the Amsler grid 71 test is undertaken while the user 12b is seeing with both eyes in a very natural way.

Figure 8:
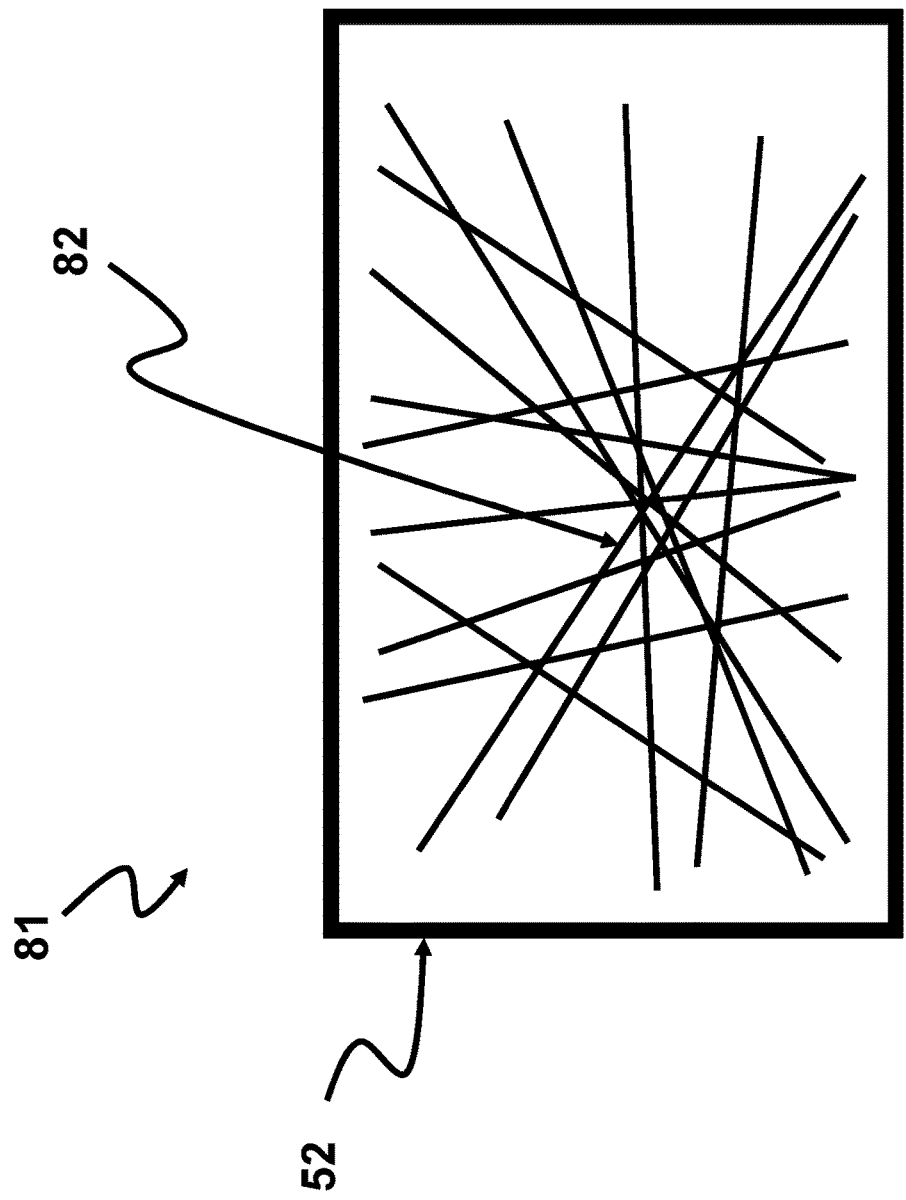
FIG. 8 shows a moving line test.

FIG. 8 shows an image of a moving line test 81. Within display screen boundary 52, moving lines 82 appear, extend, contract and rotate slowly on the display as the user 12b observes them. The lines can be in different colors and thicknesses and the background color can be varied. The user 12b looks into the center of the image and watches for anomalies such as dropped line sections, wavy lines and other distortions. When the user 12b sees an anomaly, he or she detects the location with a cursor using a mouse, game controller 112, or other human input device (or uses reference marks to indicate the location as described above with reference to the Amsler grid of FIG. 7). It may be beneficial to provide a reference image of some sort in the center of the display so that the user has a central reference point, similar to the center square 72 of the Amsler grid 71 shown in FIG. 7. However, the center of rotation of the moving lines 82 may also serve this function. The moving line test 81 is not a standard test for retinal function. It is presented here as an example of an additional test that can be run to test a user's vision for macular degeneration or other retinal disorders to ensure that results from the Amsler grid 71 are repeatable and consistent. As with the Amsler grid 71, the moving line test 81 can be varied in color, brightness, contrast, line weight, background color and other aspects.

Figure 9:
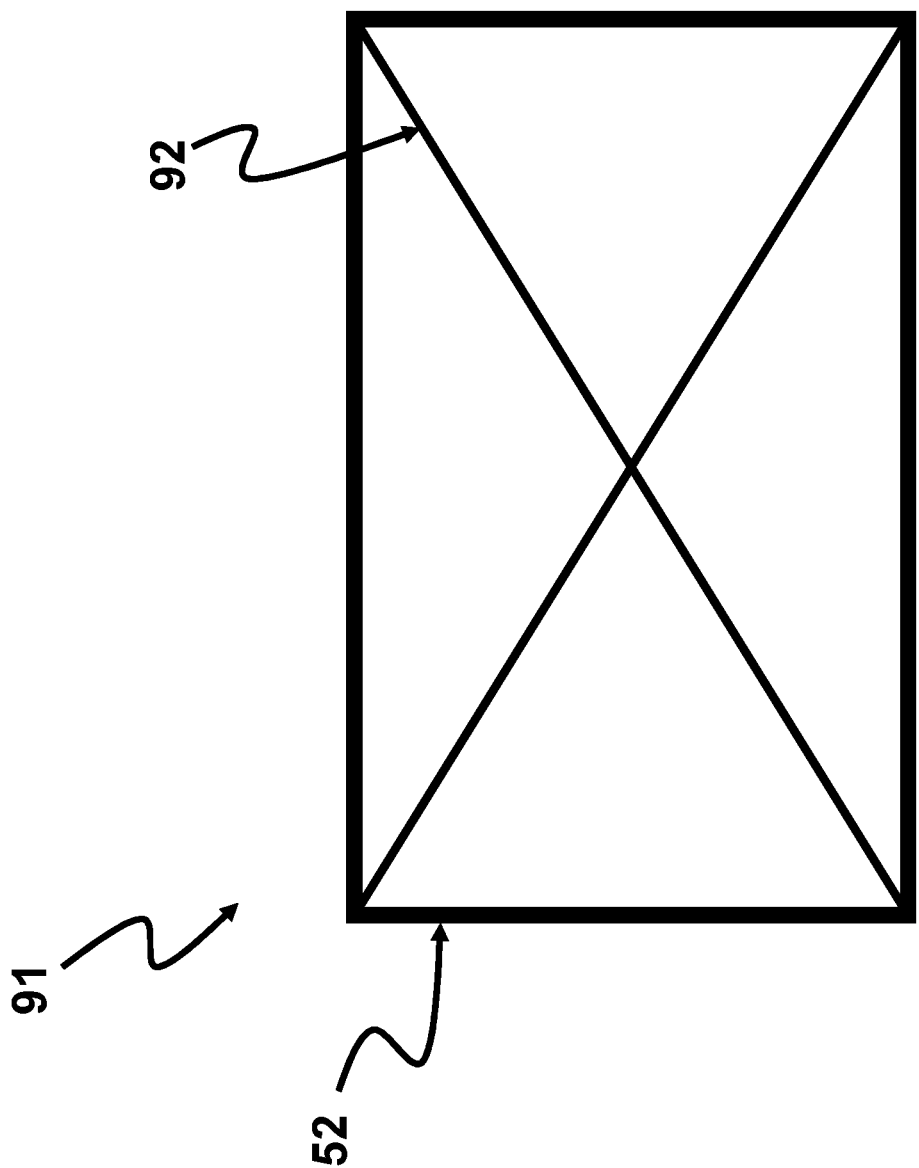
FIG. 9 shows a crosshair alignment pattern.

FIG. 9 shows a display 91 with crosshairs 92. The crosshairs 92 are diagonal within the display screen boundary 52. Other types of crosshairs, such as common vertical and horizontal crosshairs such as those used in rifle scopes, could also be used. The use of crosshairs 92 or other visual reference marks is very important in video therapy for patients with macular degeneration. Since macular degeneration results in a loss of central vision, it may not be possible for some patients to reference a single central point alone. Consequently, it is important to provide a vision reference marking in the display that allows the user 12b to align their vision using primarily their peripheral vision. Crosshairs offer benefit for this alignment versus simple markings in the display periphery as they are always visible adjacent to the central vision of the user 12b regardless of the degree of central vision that they have lost. That is, crosshairs always allow the user to make best use of whatever central or peripheral vision they have remaining whereas markings limited to the display periphery do not. Also, it should be explained that it is not enough to only properly align the binocular viewer 110b to the face of the user 12b if areas of the video display image are to correspond to specific areas of the patient's retina. Clearly, the user may rotate their eyes left, right, up or down, so it is additionally important that the user 12b look into the binocular viewer 110b directly and at a correct and consistent angle. For that reason, the user 12b should be asked to look to the center of the crosshairs 92. The moving line test 81 of FIG. 8, for example, would also benefit from crosshairs to allow the user to fix their vision in a repeatable way for the test. As previously described, a significant advantage of a head mounted binocular viewer 110b such as the one shown in FIG. 2 is that since it mounts to the head of the user 12b, it can be mounted in an accurate and consistent fashion. If used correctly, and if the video measurement includes use of crosshairs or other visual alignment marks, the vision measurement and training system 11 is then capable of concentrating on specific areas of the retina. Of course, it is beneficial that the system make some checks to ensure proper alignment before the therapy is begun. Since some areas of the retina may have been impacted by disease, it is possible to simply detect these regions and compare them to the affected regions found in prior therapy sessions. In this way, the vision measurement and training system 11 can ensure that the therapy is applied correctly. It is also possible to detect a user's natural blind spot (all human eyes have a blind spot in the retina where the optic nerve departs the eye) as an additional reference to ensure that eye alignment is correct. Detecting the natural blind spot has the added benefit that its location and size will not normally change as a user's vision disorder changes as result of progress of the disease or effectiveness of a treatment. Detecting the natural blind spot can be done by placing a feature in the display near the expected location of the blind spot and requesting that the user 12b to move it through interaction with a human input device until the feature disappears. Other ways of detecting the natural blind spot are also possible. Of course, eye tracking devices based on image processing of camera images such as through the video camera with lens 212 as previously described or other schemes to track the eyes of the user 12b can also be used. However, the added cost may not be justified. Since only measurement and training are being applied to the eye, a misalignment only means that the measurement may be faulty or the training less effective, but no immediate harm is caused (as might be, for example, if eye misalignment occurred during a laser surgery procedure). Reasonable misalignment of the binocular viewer 110b to the face of the user 12b can be accommodated by shifting the therapeutic image location on the display slightly. Large misalignments may result in the vision measurement and training system 11 advising the user to realign the binocular viewer 110b.

Figure 10:
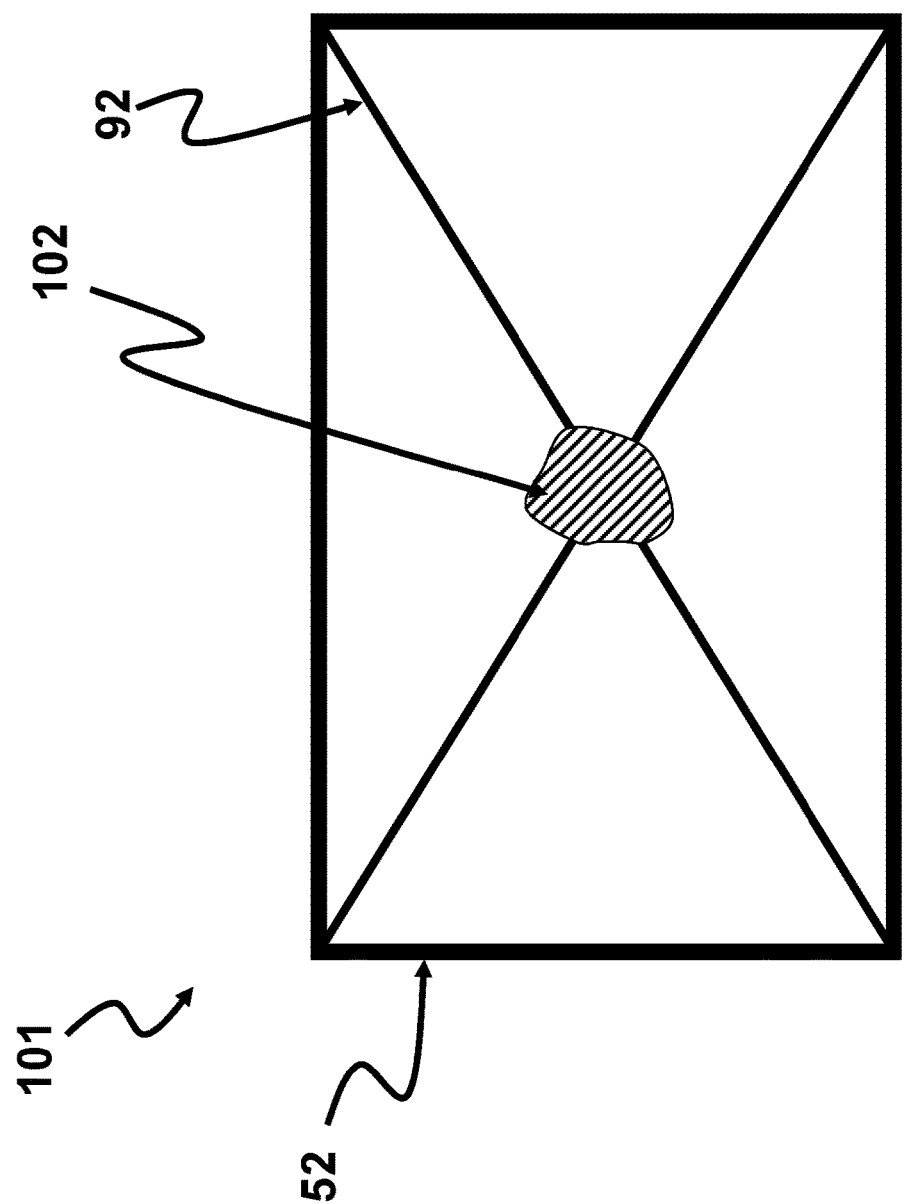
FIG. 10 shows a crosshair alignment pattern with a mapped disease-affected region of a user's eye.

FIG. 10 shows a display 101 with crosshairs 92, display screen boundary 52 and disease-affected region 102. A disease-affected region 102 is the area of the display that corresponds to the disease-affected area of the retina of the user 12b. It is noted that while the disease-affected region 102 is shown explicitly in FIGS. 10, 11, 12, 13 and 14, that in the vision measurement and training games that will be discussed later, that the region would not normally be marked in the binocular viewer 110b so as to be visible by the user 12b. That is, the disease-affected region 102 is explicitly marked in FIGS. 10, 11, 12, 13 and 14 to facilitate understanding but is not normally so marked in the actual image that a user 12b sees when viewing the images. As described above with regard to the moving line test 81 and the Amsler grid 71, a disease-affected region 102 can be first assessed by direct user 12b feedback. Later, it will be explained how such a region can be more precisely mapped. The disease-affected region 102 is shown as a single contiguous region in FIG. 10, but it is possible for patients to have multiple affected regions in their retina. In such cases, several such disease-affected regions 102 may be present. As the measurement and training regimens to follow are explained, it is important to note that all of them can be effectively applied by either treating each disease-affected region 102 separately, or to cover them in a combined fashion (for example, in a case where multiple small affected regions are present). It is also clear from FIG. 10 that the use of crosshairs 92, or other alignment schemes to direct the user 12b to look into the center of the display are beneficial as some users 12b have no significant central vision ability. In addition to substantial loss of vision in the disease-affected region 102, a user 12b is also likely to suffer loss of vision clarity in the adjacent areas of the retina and possibly across the entire scope of their vision. For that reason, it is important that all vision measurement and training include options for a variety of colors, line weights, levels of detail, brightness, contrast and other aspects so that the vision measurement and training system 11 can be controlled (either manually or self-adapted through observation of the performance through of the user 12b the measurement and/or training session) to fit specific needs.

Figure 11:
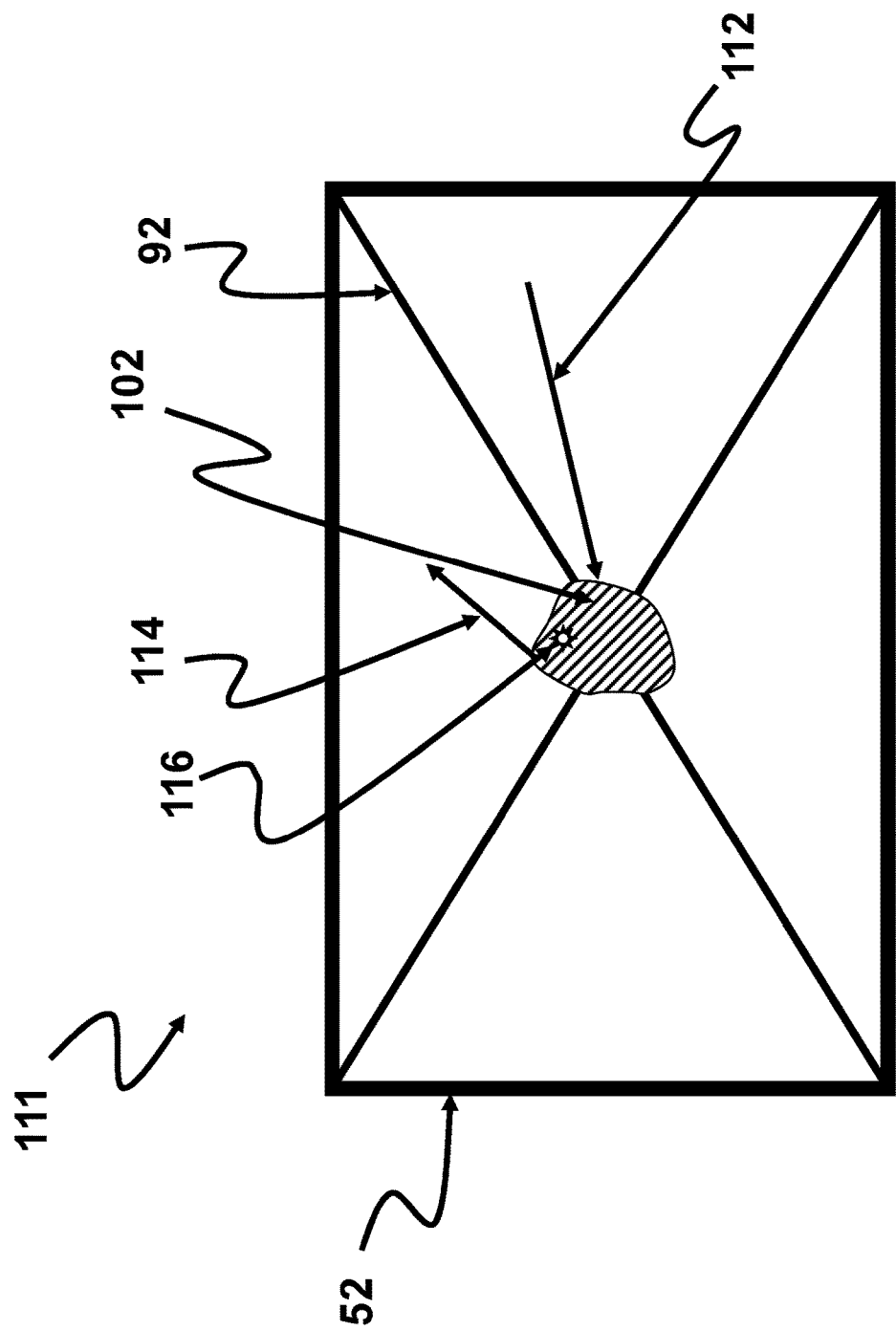
FIG. 11 shows a vision measurement or training game involving incident and departing lines, a flash is also shown in a disease-affected region.

FIG. 11 shows an image from a simple game that could be used in the measurement of macular degeneration or other retinal disorders, in particular, it shows a game involving incident and departing lines 111. As in FIG. 10, the display boundary 52, crosshairs 92 and disease-affected region 102 are shown. In addition, an incident line 112 and a departing line 114 are shown. In this game, the incident line 112 appears first as only a point near the display boundary 52 and it begins extending over time toward the disease-affected region 102. Once it enters the disease-affected region 102, a short time passes and then the departing line 114 appears first at the very edge of the disease-affected region 102 and then extends over time toward the display boundary. The departing line 114 could also begin in other areas of the display so that a complete measure of vision field could be generated. In this simple game, the user 12b simply indicates which section of the display as defined by the crosshairs 92 the departing line 114 appears in. As shown in FIG. 11, the departing line 114 appears in the upper section of the display, so the user 12b would indicate this using a keyboard, mouse, game controller 112 or other human input device. The sooner the user 12b can correctly indicate the section of the display the departing line 114 appears in, the higher the user's score. Clearly, the speed of the incident and departing lines, their color, weight, contrast, the background color, and other aspects of the game can easily be adjusted to account for the specific capability of the user 12b. And clearly, the time taken by the user to recognize the departing line 114 is an indication of his or her ability to recognize the line and, hence, is an indication that can be used to refine knowledge of the disease-affected region 102.

Since macular degeneration and some other disorders occur primarily in older patients, user 12b reaction time and physical dexterity are factors in game play. For the game involving incident and departing lines 111 shown in FIG. 11, very simple feedback based on what section of the display the departing line 114 appeared in was used, so that users 12b with limited dexterity might still play the game. As discussed before with regard to FIG. 5, reaction time can be assessed by observing the performance of the user 12b under special conditions (in this case for example, for very slow moving incident and departing lines) and can then be subtracted from other results to determine a score that is reflective mainly of vision acuity and only minimally to physical reaction time.

Once the reaction time of the user 12b and his basic ability to play the game has been assessed, the vision measurement and training system 11 can use the game involving incident and departing lines 111 to more precisely map each disease-affected region 102. Each time the user signals a departing line, the system can use the knowledge of when and where the departing line 114 was started on the display, when the user 12b signaled it and whether the user 12b correctly signaled which section of the display it appeared in to fine tune the assessment of the location and extent of each disease-affected region 102. With ongoing game play, the location and extent of each disease-affected region 102 can be more precisely mapped. Of course, some regions of the retina will have more function than others, so it is also possible to grade the vision of the user 12b based on his or her game-play ability. That is, instead of only indicating a disease-affected region 102, regions that are very badly affected might be indicated separately from regions that are only moderately or minimally affected by the disease (clearly, very many possible ways to grade vision condition as a function of location in the retina with varying degrees of complexity and benefit are possible). This information could then be used to enhance the overall system effectiveness. If the training were, for example, the game involving incident and departing lines 111, as shown in FIG. 11, game play might be concentrated in specific regions with line colors, weights, game speed and other factors adjusted to enhance the benefit of the training for the condition of the user 12b for that specific region of the retina.

FIG. 11 also includes a flash 116 of light in the disease-affected region 102 near the location of the departing line 114. In the game involving incident and departing lines 111, this flash 116 is an optional hint to the user 12b that attempts to train the vision of the user 12b. If the user 12b can see the flash, he or she can increase their score by indicating the display section of the departing line 114 possibly even before the line appears. In this way, the user 12b values the ability to observe the flash 116 and will concentrate to use and hence train, what remaining vision ability they have in the disease-affected region 102. Clearly, the color, intensity, contrast, size, location, duration, timing or other aspects of the flash 116 can be varied to provide beneficial effect to the user 12b. And as discussed above, if the condition of the retina is graded to indicate regions of the display that correspond to badly, moderately, or minimally affected areas (or other possible grades of vision performance), the flash 116 can be adapted for use in each such region. Of course, many different hints could be provided to the user 12b with similar effect to the flash 116 described here. In fact, it is also possible to provide audible hints, vibration, or other stimulus to the user 12b to draw his or her attention to some feature of the game to improve concentration on some object and increase the benefit of the training. For example, the audio stimulation of a popping sound as the departing line 114 is started might increase the attention of the user 12b to the game.

As noted above, the user 12b could have multiple disease-affected regions 102. In such a case, the game involving incident and departing lines 111 is simply extended to include all such regions. It is also noted that for the user 12b, to observe the flash 116, if it is used, it may be beneficial if the pupils of the user 12b are dilated to allow the most possible light to enter the eye. To create this situation, the game involving incident and departing lines 111, may be adjusted so that the background is either black or very dark and the finest possible lines and minimum amount of light is used in the display image that is suitable for the condition of the user 12b. This will cause the pupils of the user 12b to dilate and give the user 12b the best chance of seeing the flash 116. The concept of using a mainly dark display so that the pupils dilate is an important concept.

Another aspect of vision training for macular degeneration is parafovea training. That is, training the user 12b to make best use of the areas of the retina that are not substantially affected by the disease. The fovea is the central retina, so parafovea training is training the user 12b to use his or her peripheral vision to accomplish tasks that would normally rely mainly on the central retina. As will be discussed later with regard to FIG. 14, parafovea training is best accomplished with 3D images and stereoscopic vision, but some benefit can be achieved with simpler games such as the game involving incident and departing lines 111. In this game as described, the user already watches the incident line 112 and departing line 114 as they move through the sections of the display that do not correspond to the disease-affected region 102. If the game is extended so that the point where the departing line 114 exits the display provides a hint for where the next incident line 112 will appear, the user 12b is then benefited by closely observing where the departing line 114 exits the display (for example, the next incident line 112 might first appear diametrically opposed to where the last departing line 114 exited, but many other schemes are clearly possible). In this way, the user 12b is benefited to make use of their peripheral vision and parafovea training is achieved. Clearly, much more sophisticated enhancements are possible. Enhancements to a game to extend the interest of the user 12b to the peripheral areas of the display may be quite desirable.

It is also noted that vision training for patients with retinal disorders that do not go to the lengths described above to ensure good alignment of the video display to the patient's retina and may also not attempt to assess what parts of the retina are affected by macular degeneration are possible. However, there are many millions of photo receptors in the retina, so there is a large benefit to attempt to concentrate training where the most benefit may be received. And for some patients, games that fail to first assess the patients vision ability could result in simply displaying games that are impossible for the patient to play with any measure of success. One strategy for such a situation, that may also be useful for very extreme cases of macular degeneration or for patients with very poor motor skills or dexterity is to play a game that varies the game play from location to location on the display so that the patient can engage and play the game for at least a part of the therapy session.

Figure 12:
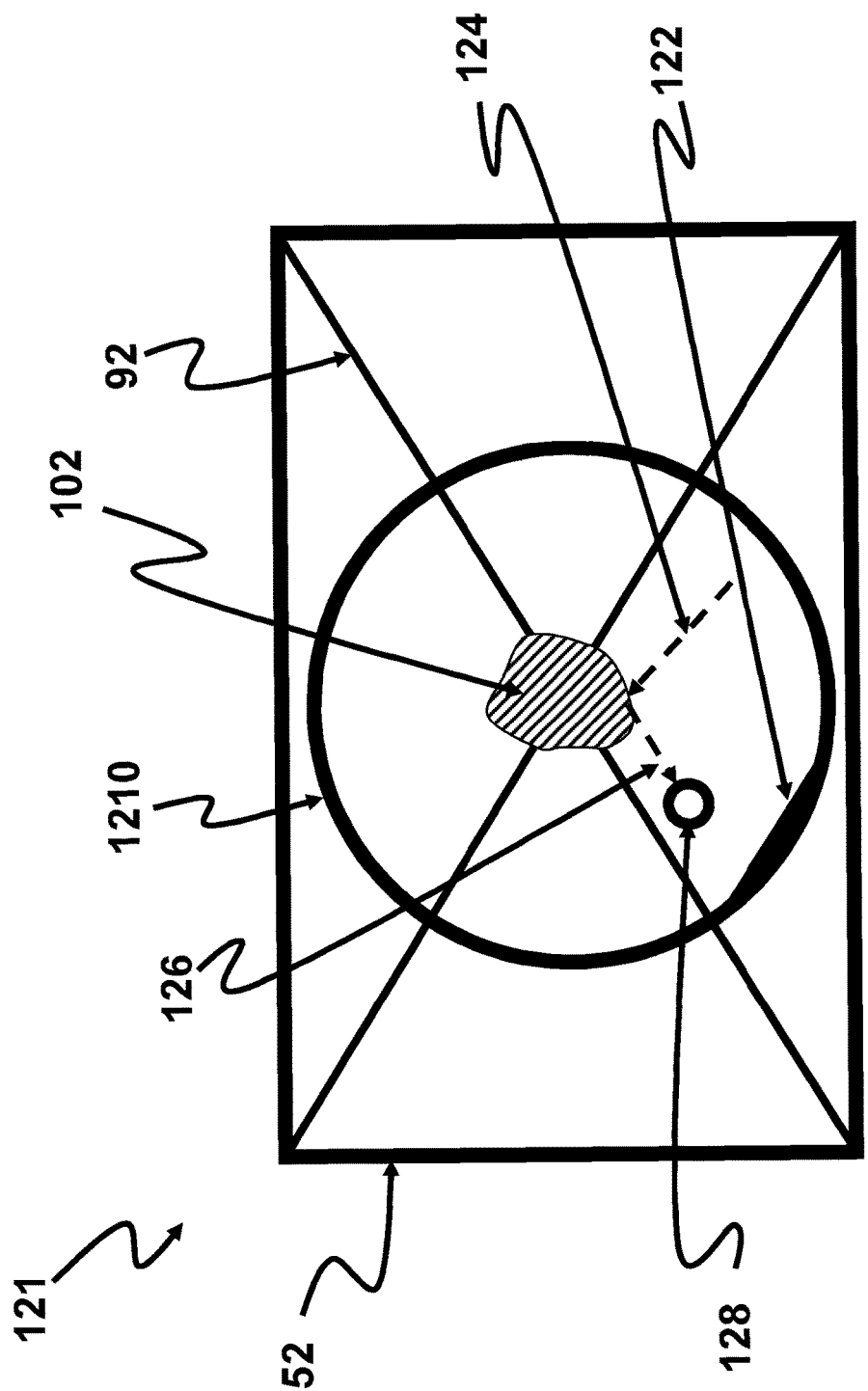
FIG. 12 shows a vision measurement or training game based on a circular form of computer tennis.

FIG. 12 shows a display image of a game based on circular tennis 121. In the game, a moving tennis ball 128 is deflected from a disease-affected region 102 and a flat section 122 of a circle 1210. The user 12b need only rotate the circle 1210 so that the flat section 122 contacts the tennis ball 128. This operation is simply accomplished through many different possible human input devices. Note that the circle 1210 in the game based on circular tennis 121 provides a reference for the user 12b to align their eye to the display in addition to the crosshairs 92. The incident trajectory 124 and reflected trajectory 126 may be responsive to the point where the tennis ball 128 strikes the flat section 122 and a disease-affected region 102. In such a case, the game play could be more varied and interesting. Clearly, if a patient has multiple disease-affected regions 102, the game based on circular tennis 121 might encompass all of them inside the circle 1210 and treat them together, or otherwise treat them separately and play around each of them in sequence. It is clear that in the game based on circular tennis, the ability of the user 12b to play a specific situation of the reflected tennis ball 128 allows knowledge of the disease-affected region 102 to be improved. It is noted incidentally that FIG. 12 also shows crosshairs 92 and display screen boundary 52.

Figure 13:
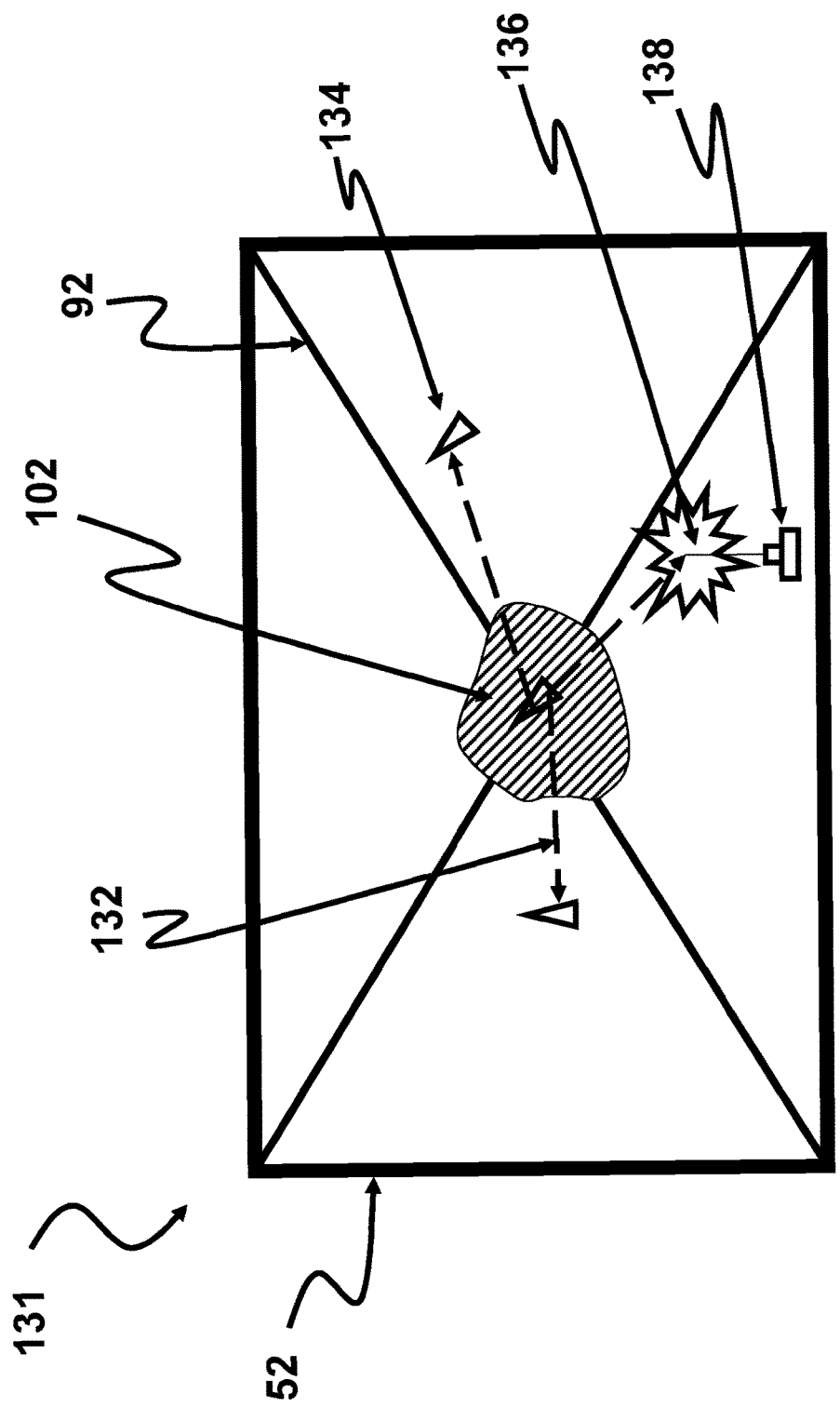
FIG. 13 shows a vision measurement or training game based on firing a gun at enemy objects emanating from a disease-affected region.

FIG. 13 shows a display image of a game based on shooting enemy objects 131. In this game, enemy objects 134 emanate from a disease-affected region 102 along various departing trajectories 132. The user 12b controls the horizontal position of a gun 138 and shoots at the enemy objects 134 to create explosions 136 that destroy them. The more enemy objects that are destroyed, and the closer they are destroyed to a disease-affected region 102, the higher the score. And clearly, the ability of the user 12b to play can be used to enhance knowledge of the disease-affected region 102. Here, if multiple disease-affected regions 102 are presented, enemy objects 134 might simply deploy from all of them, or they could be treated in sequence and other possibilities also exist. It is noted incidentally that FIG. 13 also shows crosshairs 92 and display screen boundary 52.

In FIGS. 11, 12 and 13, simple games were illustrated that showed how a user's interest could be drawn to increase use and concentration on certain areas of the retina and how game plan ability can be used a measurement capability to assess vision performance and refine knowledge of the disease-affected region 102. In each case, a very wide variety of color schemes, contrast, brightness, feature size, game speed and other characteristics were possible to accommodate a given user's needs and ability to play an interactive game. Each game can attempt various colors, line widths, contrast and all other parameters and monitor the user's progress to determine the limitations and capability of the vision of the user 12b. It is also possible for each game to be played separately for each eye or to combine play so that while both eyes view much of the same image, that one eye only will see some important aspects that allow the vision measurement and training system 11 to measure and train each eye separately or together. That is, some special features in the image are presented to only one of the eyes of the user 12b and those features are simply not displayed on the side of the binocular viewer 110b for the other eye. Additionally, games could be devised using 3D stereoscopic vision images so that items only intended for one eye to see could be situated in the 3D image so that only one eye would normally see them as was described with regard to FIG. 6. Clearly, a very wide variety of games are possible.

Figure 14:
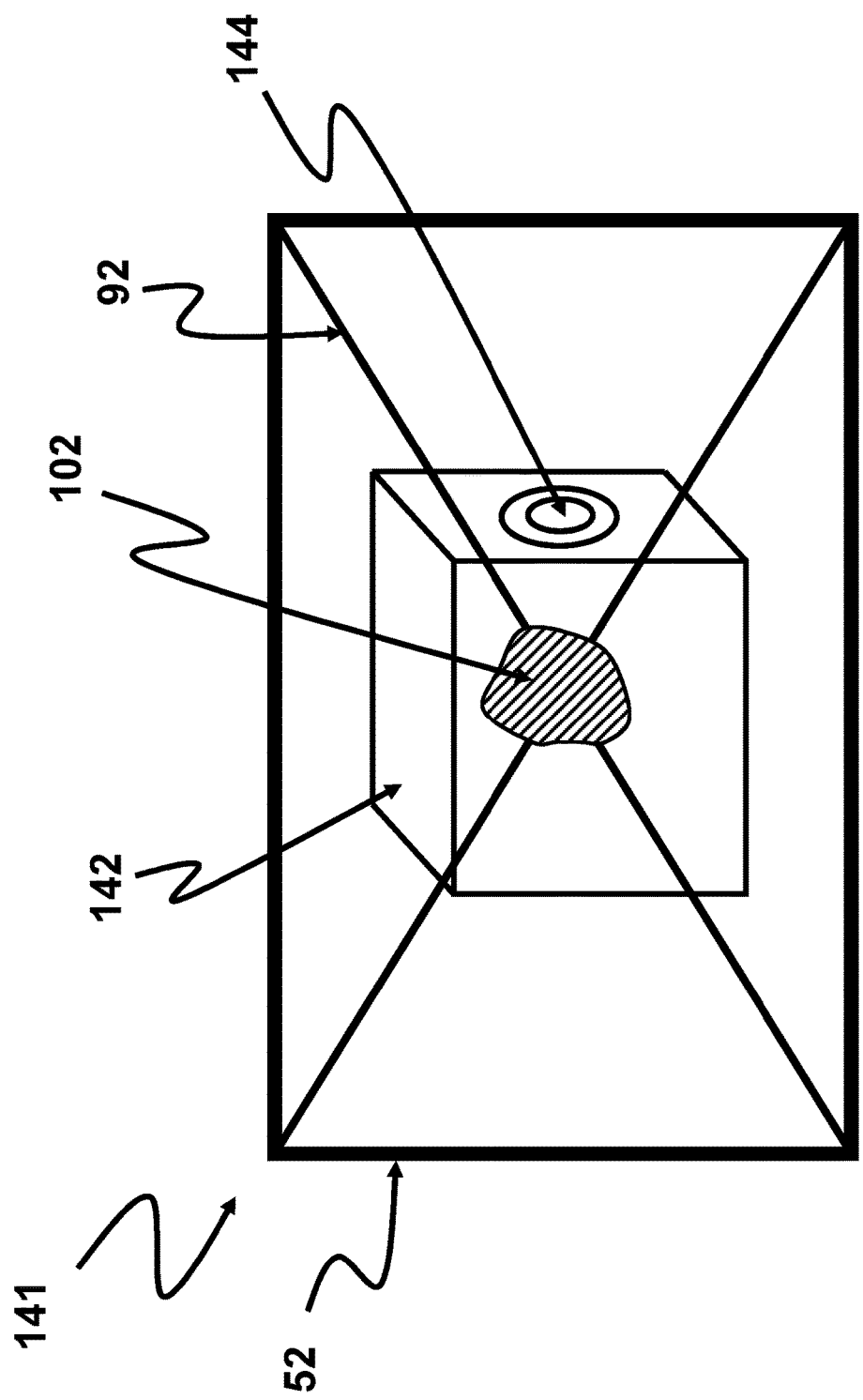
FIG. 14 shows a view of a three-dimensional, or stereoscopic, image fitted around a disease-affected region. The surface of the stereoscopic image includes a target that the user can interact with for parafovea training.

FIG. 14 shows a representation of a game with three dimensional object 141. The display boundary 52, crosshairs 92 and disease-affected region 102 are all visible. The three dimensional object 142 is a box that surrounds the disease-affected region 102. The game with three dimensional object 141 is presumed to be played in stereoscopic vision so that the user 12b sees a very real three dimensional object 142 that has true perspective and parallax. In one possible embodiment of the game with three dimensional object 141, the three dimensional object 142 rotates and the user 12b plays the game by interacting with images on the faces of the object. One possible such image is the target 144 shown on the right face of the three dimensional object 142 in FIG. 14. As each face rotates into view, the user 12b first sees the target 144 in his or her peripheral vision. In this way, the vision acuity of one of the eyes of the user 12b can be assessed separately and the training routine is directed to the peripheral area. Depending on whether the three dimensional object 142 rotates to the left or right, one eye or the other will see each face first. The use of such a game with three dimensional object 141 is helpful for patients who have lost some vision function (such as the disease-affected region 102) and need to learn to use their peripheral vision more extensively to perform every day tasks. This is very difficult for many patients as their neural functions have always depended on central vision through the course of most of their lives. It is also very clear that using three-dimensional stereoscopic vision images through a binocular viewer 110b is dramatically advantageous since the user 12b needs to view images that are very close to those from natural vision in the real world. As the capability for adaptive focal depth explained with regard to FIG. 3A and FIG. 4 is a further ability to help the user 12b feel they are in the real world, inclusion of adaptive focal depth into the game with three dimensional object 141 is also a clear advantage. Training a user 12b to use their remaining peripheral vision function is sometimes referred to as parafovea training.

Parafovea training with a binocular viewer 110*b* with adaptive focal depth capability also has other benefits. The ability to produce more natural images should result in better comfort for some users 12*b*. Indeed, using only one eye for extended periods, as might be attempted with other approaches to computerized parafovea training, may result in user 12*b* discomfort and introduces the complication of binocular function, convergence and fusion not being a specific part of the training session. Lack of binocular images would leave the key ability to combine (fuse) images together from each eye to create a true sense of space apart from the training. Hence, user 12*b* comfort and the ability to provide real binocular training are substantial benefits to use of a binocular viewer 110*b* with adaptive focal depth.

As with the other game examples, the game with three dimensional object 141 can be altered to use different sized objects, different rotation speeds, different colors, different contrast, different brightness and other variations. Clearly, a similar concept can also be applied to many other possible gaming environments. For example, instead of viewing a rotating box, the game could comprise a view from the cockpit of an airplane that is flying through an interesting region (such as a canyon or city central region). As the airplane travels through the region, images come into view first in the peripheral region of one eye or the other as the plane turns and rotates. Hence, the use of any game play that causes sequences in a 3D stereoscopic vision display to preferably demand the use of peripheral vision and where this effect is used to assess vision acuity and/or to provide training, is a part of this patent application. Clearly, the concept described can be applied to cars traveling on a road (or off road), a person running through the jungle (or anywhere) and perhaps an infinite number of environments and situations. One common environment that is used already in gaming that could be easily adapted to the video game environment described here are the so-called "first-person shooter" games. In these games, the user is effectively behind a gun and is going through an interesting environment hunting for enemies. Normally, there are many turns and twists so that the three dimensional environment would have many areas that would come into first view in the peripheral vision region if a real stereoscopic vision display is used, such as the binocular viewer 110*b* shown in FIG. 2.

Figure 15:
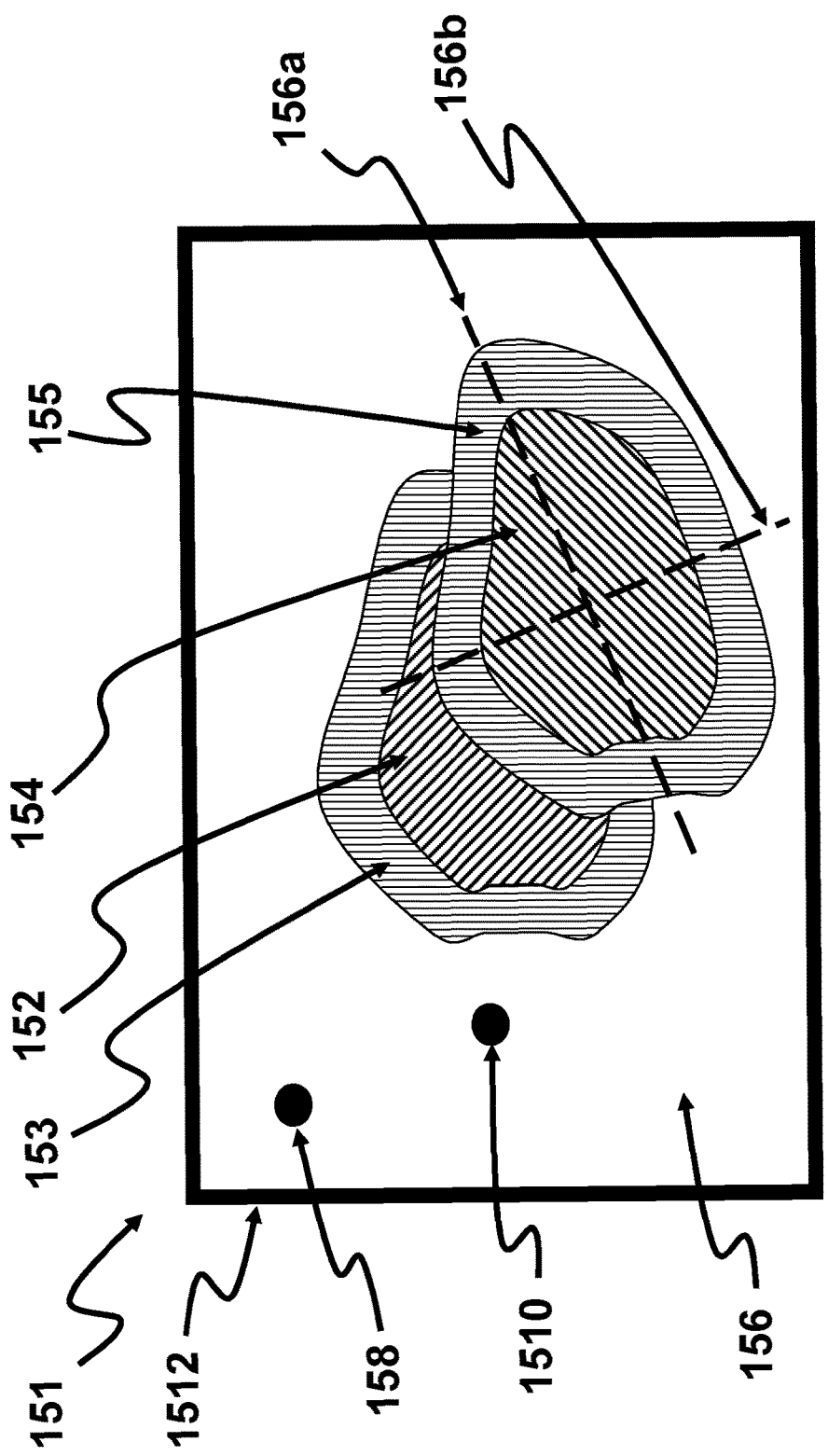
FIG. 15 shows how data from multiple games or the same game conducted at different times can be combined to create a single database.

FIG. 15 shows a graphical representation of a vision field database 151 for one or both of a user's eyes. How misalignment of the binocular viewer 110*b* can be detected and corrected will be described. It will be assumed initially that eye tracking using the camera with lens 212 in FIG. 2 is not activated. Severe vision loss data region 152 corresponds to an area of the vision field of the user 12*b* in which vision was measured to be severely impaired or nonexistent. Moderate vision data region 153 corresponds to an area of the vision field of the user 12*b* in which vision loss was measured, but some vision function remains. And normal vision data region 156 corresponds to an area of the vision field of the user 12*b* in which normal or nearly normal vision function was measured. Note that the vision field test limit 1512 is not the same as the display screen boundary 52 shown in some prior figures. The reason is that the user 12*b* can be directed to look toward one of the screen boundaries as his or her vision field test is extended in the opposite direction. For example, if the user 12*b* is directed (normally with a visible stimulus such as a target or other object) to look toward the far right, his or her peripheral vision toward the left can then be measured further than it could if the user 12*b* simply looked straight forward. And this technique can be repeated in every direction. Hence, the vision field test limit 1512 can substantially exceed the display screen boundary 52. Clearly, many possible vision scoring schemes and many levels of gradation of vision function are possible versus the simple three regions (normal, moderate vision and severe vision loss) demonstrated here. One simple measure is simply to record the number of correct versus incorrect user 12*b* responses in a given region of vision field using one of the tests explained earlier, such as the game involving incident and departing lines 111 in FIG. 11. In this way, the areas of vision function would be a simple percentage and could then be organized into specific gradations of vision function or could even be stored in the database as a continuum of values. The blind spot data region 158 is the representation of the natural blind spot (corresponding to the place where the optic nerve departs the eye) of the user 12*b*. It is important to note that the normal vision data region 156, the moderate vision data region 153, the severe vision loss data region 152, and the blind spot data region 158 are representations of stored data in a database that might be from a single test taken on the user 12*b* at a prior date or time, or could perhaps be composite data that has been derived from the combination of multiple prior tests. That is, the data regions shown in FIG. 15 might be single test results or averages, weighted averages, or other combinations of past data from multiple tests or tests taken at multiple times.

The severe vision loss new measurement region 154, the moderate vision new measurement region 155, and the blind spot new measurement region 1510 all correspond to new measurement data collected in an ongoing or past measurement session that are to be combined with the existing data. It is very clear in FIG. 15 that while the overall shapes and sizes of the vision loss new measurements correspond to those from the data in the database, that they are misaligned. This is also clear from the location of the blind spot new measurement region 1510 versus the blind spot data region 158. If the new measurement is ongoing, it is possible to alert the user 12*b* through the vision measurement and training system 11 that a misalignment exists and that the binocular viewer 110*b* should be adjusted. Of course, even with careful adjustment, the user 12*b* will only be able to achieve an approximately correct alignment of the viewer to his or her face. Consequently, it is also important that small misalignments be corrected automatically through scaling, shifting, rotation or other possible transformation of the data records corresponding to the measurements. In the example of FIG. 15, the new data horizontal axis 156*a* and new data vertical axis 156*b* provide some reference for the amount that the new data should be rotated (as shown it would be clockwise) before being shifted to correspond to the alignment of the existing data. Of course, the new measurement data will not normally correspond perfectly to the existing data since the vision of the user 12*b* may well have changed since the existing data was taken. Consequently, the new measurement data should be rotated, scaled and/or shifted (these operations might take place in any order) and then correlated with the existing data to achieve the best overall correlation before being combined with the existing data.

Of course, a single measurement session for vision field can involve many thousands of data points, so it can be frustrating if the user 12*b* is asked to realign the binocular viewer 110*b* and rerun the test due to misalignment. Consequently, it is beneficial to organize the test games so that basic alignment data can be collected in the first few minutes of game play. That is, some key alignment measures relating to the blind spot of the user 12*b* and vision loss regions can be collected quickly to provide an adequate indication that the binocular viewer 110*b* is sufficiently accurately aligned that the test can go on and any remaining misalignment can be corrected by shifting, rotating and scaling the data as described above. This concept can be extended to include occasionally revisiting the issue of viewer alignment in the course of the game to take some basic measurements and ensure the viewer alignment has not shifted. In the event the viewer alignment has shifted, the measurement data can be rejected and the user 12*b* advised to restart the test and to be more careful about alignment.

The concepts regarding alignment as explained above with regard to FIG. 15 can easily be extended to include the situation in which eye tracking measurements are taken using the camera with lens 212 shown in FIG. 2. In the case that eye tracking is used, the vision measurement and training system 11 will have accurate data regarding the direction each of the eyes of the user 12*b* are looking when each measurement is taken. Consequently, the user 12*b* only needs to be alerted if the binocular viewer 110*b* has been poorly aligned when the test begins and the eye tracking capability alone is normally adequate to do this (that is, no specific testing need take place as the eye tracking capability will directly report eye alignment). And, each measurement data point can be either corrected for misalignment or discarded if eye alignment was sufficiently poor that the measurement is of suspect quality. Regrettably, eye tracking systems can be rather expensive and are not normally included in commercially available binocular viewers, hence, the techniques outlined above to deal with eye alignment are beneficial for development of low-cost systems. It is also possible to combine the alignment detection and correction techniques described above with the use of eye tracking. This might be especially important if the user 12*b* moves his eyes so quickly that the eye tracking system is unable to react and the movement, while unnoticed by the eye tracking system, results in erroneous data.

As previously noted, many vision disorders need to be carefully monitored and tracked as a worsening condition can quickly lead to blindness if not treated. In the case of macular degeneration, for example, wet macular degeneration in which actual bleeding of the retina occurs may develop and should be treated very quickly. If such a situation arises, the vision measurement and training system 11 would analyze the existing data regions of FIG. 15 and find that they correlate below an acceptable threshold with the new measurement regions. The level of acceptable correlation can be set by a care provider and may depend on many factors including the condition, age and past treatment history of the user 12*b*. The level of acceptable correlation may also be adapted to the length of time that is spanned from the time the existing data regions where updated to the time that the new measurement data was collected. In any case, if the new measurement data and existing data for the user 12*b* fail to correlate with each other to an acceptable level, the user 12*b* can be alerted by the vision measurement and training system 11 to seek help from a professional care provider.

The vision measurement and training system shown in FIG. 1 is clearly capable to build a rather sophisticated database of the vision capability of the user 12*b* for each of the eyes of the user 12*b*. Additionally, the database may include information entered by a doctor or care provider based on their diagnosis of the user 12*b*, information input by the user 12*b* regarding their condition and from the results of the basic tests such as the Amsler grid 71 test and also from information gained by the performance of the user 12*b* in game play for games such as the game involving incident and departing lines 111. Information in this database can be reported to a doctor or care provider and can be formatted to be highly useful for them. The database information can also be used to adapt training or measurement by the vision measurement and training system 11 automatically. Clearly, in such a database, it may be beneficial to give different weight to certain information depending on how it was received. For example, specific information from an eye doctor may be considered absolute and to be trusted regardless of other information the vision measurement and training system 11 may determine. Information received from user 12*b* input such as the Amsler grid 71 test may be treated with some suspicion unless it is reasonably consistent with information from the eye doctor or other sources. And information received from the results of game play might only be trusted once verified to be consistent with other information sources. Clearly, through a reasonable system that includes information regarding confidence factors related to all information received, it is possible to build a vision measurement and training system 11 that provides benefit to a user 12*b* without being responsive to misguided, incorrect, or even possibly malicious information it may receive. However, since the system is providing only measurement and training, there is little risk of damage to the user 12*b*. And, if information from multiple sources is not sufficiently consistent to allow the system to confidently provide useful results, the vision measurement and training system 11 may alert the user 12*b* to this condition with directions that the user's eye doctor be consulted.

It is also clear that the video images and displays shown herein all offer the possibility for a multitude of colors, brightness, contrast, line weights, game speed and other adjustments to the specific condition of the user 12*b*. With such a wide variety of adjustments, it is possible for adjustment of the system to become burdensome, especially for a doctor who is beginning a new user 12*b*, for example, on the vision measurement and training system 11. However, with a reasonable beginning point, it is possible for the system to self-adapt all these settings based on the responses and game play results of the user 12*b*. Some very simple initial settings may be included in the vision measurement and training system 11 to simplify this situation. For example, the level of macular degeneration or other disorder might be input simply as minimal, moderate, or severe and the ability of the user 12*b* to play with good dexterity might be characterized as simply poor, fair, or good. In this way, basic information is provided to the vision measurement and training system 11 with which it can adapt suitably for the user 12*b*.

Figure 16:
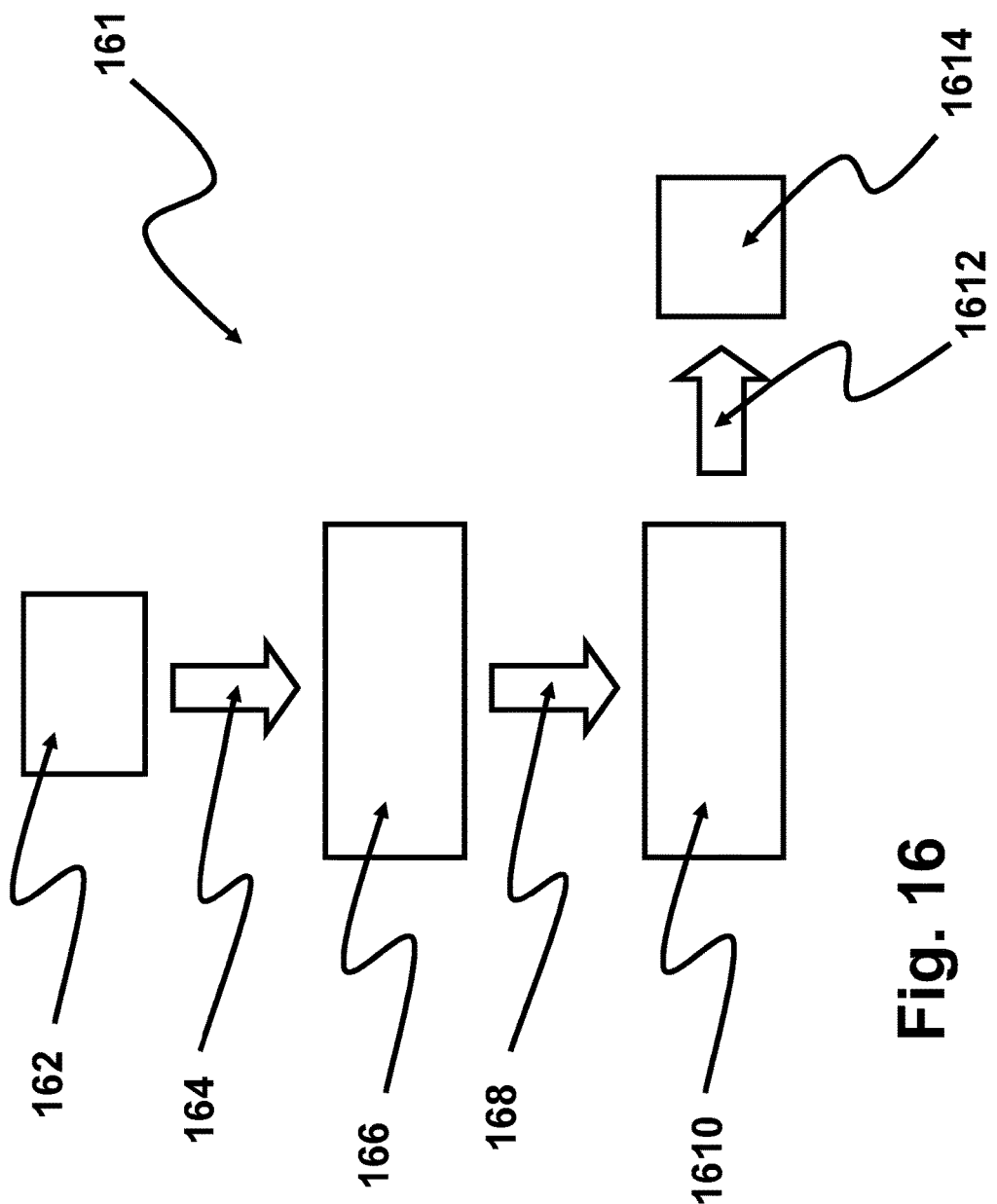
FIG. 16 shows a flow chart of the data processing functions that could be used to modify a conventional computer application to incorporate vision training.

While specific measurement games would normally be used for vision measurement, vision training can possibly also make use of images that are commonly used in every day life so that the user 12*b* can take benefit from vision training in the course of their normal every day activity. In FIG. 16, a flow chart is shown that outlines some of the steps needed to create images suitable for vision training using computer images used with common computer applications 161. The example of FIG. 16 is for a vision training regimen concentrating on focusing ability, but it is clear that many possible regimens could be devised in a similar fashion. These common applications include spreadsheets, word processors, internet browsers, photograph editing tools and other computer applications. The process begins with the original computer application software 162. First, a software process to create a 3D version of the software 164 is applied to the computer application software 162 to create a 3D version of the display images the computer application software 162 produces. The result is a 3D display version of the computer application software 166. Since most computer applications are 2D (two dimensional), this might involve taking some assumptions about the distance of various objects in the display image, or might only involve creating the correct parallax and focal depth so that the image would appear in 2D at a focal depth that could be varied over time (note that even though the image would appear 2D in this case that the binocular viewer 110b could still be used). The resulting software would then be subjected to a software process to vary distance and location of images in the software application 168, resulting in a version of the computer applications software including vision training capability 1610. Finally, a software process to control user specific characteristics 1612 such as color, line width, preferred focal depth and other aspects is applied to create a version of computer application software ready to be displayed 1614. The software process to control the user specific characteristics 1612 may also involve using software to vary the parallax and focal depth of various objects in the image if a full 3D image is created or to simply vary the parallax and focal depth of the full image at once if a 2D image is to be created. As an example, consider a computer user desiring vision training at various focal depths viewing a document in a common word processing application. The process of FIG. 16 could create a 2D version of this application suitable for display on binocular viewer 110b, it would then generate the parallax and focal depth information needed by binocular viewer 110b to generate the 2D image at varying distances. Finally, it would generate a sequence of distances that the resulting 2D image would be viewed at to create a vision training routine. The length of time the image stayed at a given distance, whether it changed gradually from closer to further away or moved suddenly, lateral or vertical movement of the image over time and other aspects of the image could all be controlled. Since the user would normally have access to a human interface device such as a keyboard, mouse, or other interface when using a computer application, the vision training could also be responsive to the user's wishes to speed up, slow down, stop or otherwise alter the routine. For example, a user 12b reading a document over the internet might want each page to appear at a different distance, but might not want the system to vary the distance in the course of his or her reading each page. Another example could be a user 12b viewing technical drawings that might desire the routine to stop briefly on command so that specific features could be studied in detail without distraction.

The vision training system using computer images used with common computer applications 161 shown in FIG. 16 is illustrated as a series of discrete processes for illustrative purposes. In most embodiments, it is likely that continual or otherwise different data processing strategy would be applied in which images from the original computer application software 162 would be intercepted before being sent to the computer display and would be altered as needed to create the necessary display and control information for the binocular viewer 110b. Of course, there are many (perhaps infinite) possible variations for how this processing could be undertaken without deviating from the scope of this patent application.

It is also clear that the discussion above on the vision training system using computer images used with common computer applications 161 can be extended to include video images generated by other means than computer applications. For example, television images could also be transformed in a very similar way and could also be incorporated into a vision training system. Video from television, video tapes, DVDs, camcorders, digitally recorded video, compressed video, still images, mobile television, internet TV and other sources could all be used in a similar fashion and their use as video source material that can be manipulated to create eye exercise therapy materials is considered a part of the disclosure. This will be explained further later and is illustrated for the specific case of television signals in FIG. 17.

It is also noted that if a camera system were included in the vision measurement and training system 11, the captured images could be subjected to the process of FIG. 16 or a similar process so that they could also be used as part of a vision training routine. An example of this would be a person reading a text book. As each page is flipped, the camera could capture the image and the vision measurement and training system 11 could provide an appropriate version of it for training purposes.

Figure 17:
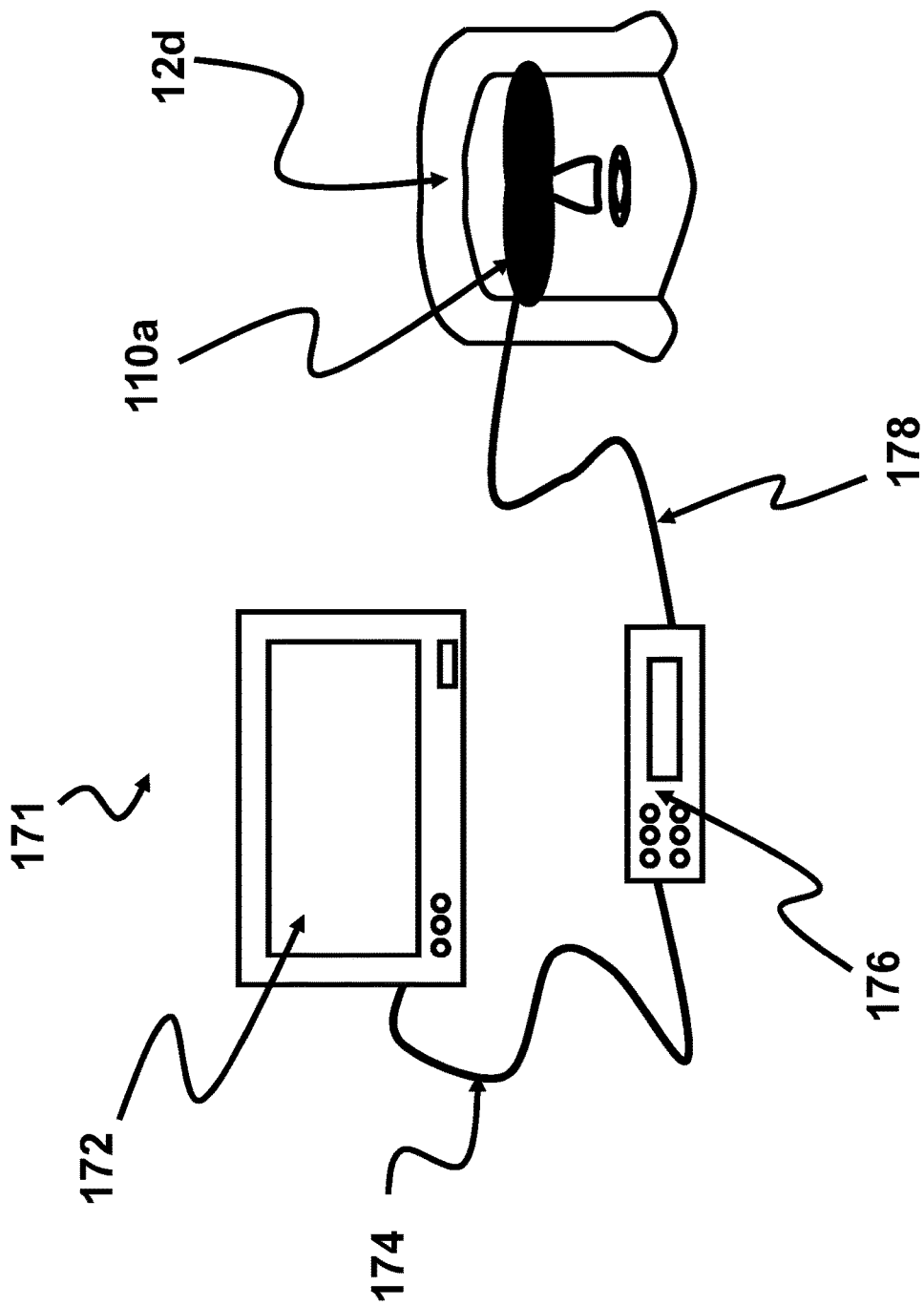
FIG. 17 shows a television and control box creating video images for a user based on data gained from vision measurement games.

FIG. 17 shows a possible embodiment of another system that could provide benefit to persons with vision disorders. In FIG. 17, an enhanced television system 171 is shown, in which a television 172 is connected to a control box 176 through an electrical cable to control box 174. The control box 176 is connected to binocular viewer 110a through an electrical cable 178. The television 172 in FIG. 17 is shown mainly for illustrative purposes since, as long as the television signal or some other commonly available video signal is available in some fashion the presence of an actual television 172 is optional. In the enhanced television system 171, the control box 176 operates on the television or other video signal to create beneficial images. Note that the control box could be programmable so that information it receives from a care provider, the vision measurement and training system 11, or other sources could be used to adapt the creation of images in the control box 176 to optimize the video a given user 12d receives. The enhanced television system 171 shown in FIG. 17 may be especially beneficial to users who are unable to operate a computer system, unable to operate a game controller (for example, patients with poor coordination, arthritis or other conditions affecting their physical ability) or who normally watch television or other video for many hours each day.

The enhanced television system 171 is capable to create a wide variety of images. For example, a user 12d with macular degeneration may benefit from an image that is distorted so that some of the image that would normally fall into the center of the display is stretched so that more of the interesting detail falls into the periphery of their vision (parafovea). In addition to allowing the user 12d to better view the image or video, this technique may also be beneficial as parafovea training. If the control box 176 is provided information about a specific condition of the user 12d, this stretching of the image could be adaptive to their specific needs. Other alteration of the incoming video signal is also possible. Simply making the image in the disease-affected region 102 brighter, higher contrast, or altering the composition of colors in it might be helpful for users 12d with only mild macular degeneration. Use of edge enhancing video filters to create bolder edges and to eliminate fine details that create a confusing image could be applied. Detecting motion in the video stream, as is often done in video compression technology and using that information to crop the signal and dedicate more of the display to the changing and more interesting part of the video image sequence could be beneficial. And certainly, a combination of cropping, stretching, enhancing, or otherwise altering a video signal to make it most useful and therapeutic to a user 12d is possible.

Of course, the enhanced television system 171 of FIG. 17 can be implemented in many possible ways. The control box 176 could be integrated into the television 172 or the binocular viewer 110a. It is also possible that the complete system could be integrated into the binocular viewer 110a. And, of course, while the binocular viewer 110a provides key benefits as already described herein many times, it is possible to use some of the techniques described with other display technologies. Many other configurations including the use of image source files, television and other video and image files and signals of all possible formats are considered part of this patent application. Also, it is clear that the control box 176 could receive vision measurement data from the vision measurement and training system 11 or from other source through a very wide variety of methods including computer disks, tapes, data cards, internet file transmission, wireless transmission, wired transmission, or many other methods.

It is also noted that the vision measurement and training system 11 described herein can be combined with other forms of eye therapy. For example, massaging the eyes before or after using the system might be beneficial. It is also possible that drugs could be used to relax the eyes, stimulate or otherwise condition the retina or macula, or otherwise put the eye into a condition that makes vision training more effective. Hot or cold treatments combined with vision training and or the use of physical exercise (e.g., running, stationary bicycle, etc.) by the user before, after, or during the eye exercise therapy may also benefit the therapy and produce better or more rapid results. And of course, even other techniques such as acoustic, electrical, chemical, or other stimulation of the eye, or possibly the optic nerve might also be found beneficial in conjunction with the vision training techniques described herein. It is noted also that use of a head mounted display such as the binocular viewer 110b shown in FIG. 2, or another type of display that contacts the users 12b face, could allow for the display to include elements of a combined therapy. A strobe to provide bright flashes of light, a source for ultrasound, vibration, or audible sound to massage the eye, a heater, vibrator, fan, water jet, or other function could be incorporated into such a viewer to augment the training regimens presented herein.

An additional possible combined therapy is the exercise of the muscles that control the direction and rotation of the eye. There are several muscles around the eye that allow the eye to look left, right, up, down, etc. Normally, most of the techniques and therapies described herein will be done with the patient looking forward and maintaining alignment of their eye to crosshairs 92 or other visual reference marks. However, vision training to treat strabismus, diplopia and some other disorders involves training of the muscles that control the direction of the eyeball. Hence, causing a user 12b, to look sharply to the left, right, up, down, etc. (could also be at angles) or to roll their eyes in their eye sockets may be beneficial for some vision training. Tension from the eye steering muscles might also be beneficial in some therapies. For example tension from the eye muscles (especially tension from them when the eye is turned in the socket so that the tension tends to pull outwardly on the side of the eye) might allow the eye to resume a more natural shape instead of the elongated shape that is typically associated with myopia. It is noted that some forms of vision yoga are based on looking in certain directions and then returning to normal vision. Providing such a therapy is possible by simply moving the objects of interest on the display to the far display periphery and possibly removing the crosshairs or other vision reference marks from the display (and possibly alerting the user 12b in other ways as well, such as telling them using a sound system or writing it on the display). In cases where the physical construction of the binocular viewer 110b may not provide a sufficiently wide field of view to cause the user to look as sharply in a direction as desired, the user 12b might be simply directed (through audible, visual, or other methods) to perform the exercise (for example, "turn your eyes as sharply to the right as you can"). It is also possible to add features inside the binocular viewer 110b housing that could assist the user 12b to perform such a regimen. For example, a small light on the right side of the viewer such as lights 28 or 214 might come on when the user 12b is asked to look to the right to give the user 12b a reference to look at (and similar lights could be included for up, down, left, right, lower right, upper left, etc.). As noted previously, some commercial binocular viewers on the market today incorporate position sensing ability. If such capability is available, it provides another method to ensure that the user 12b is really rolling their eyes in the eye sockets and not simply turning their head in response to a command. And finally, some eye disorders specifically associated with the eye steering muscles, such as vision convergence problems, may benefit substantially from a training regimen as described that causes the user 12b to direct or roll their eyes in a certain way. And it should be clear, that with the binocular viewer 110b and the methods for measuring vision and adapting training to the condition of the user 12b that have been described herein, it is also possible to assess problems with the eye steering muscles, assess progress and adapt training so that the user 12b receives the most beneficial therapy possible for eye steering muscle related conditions.

Figure 18:
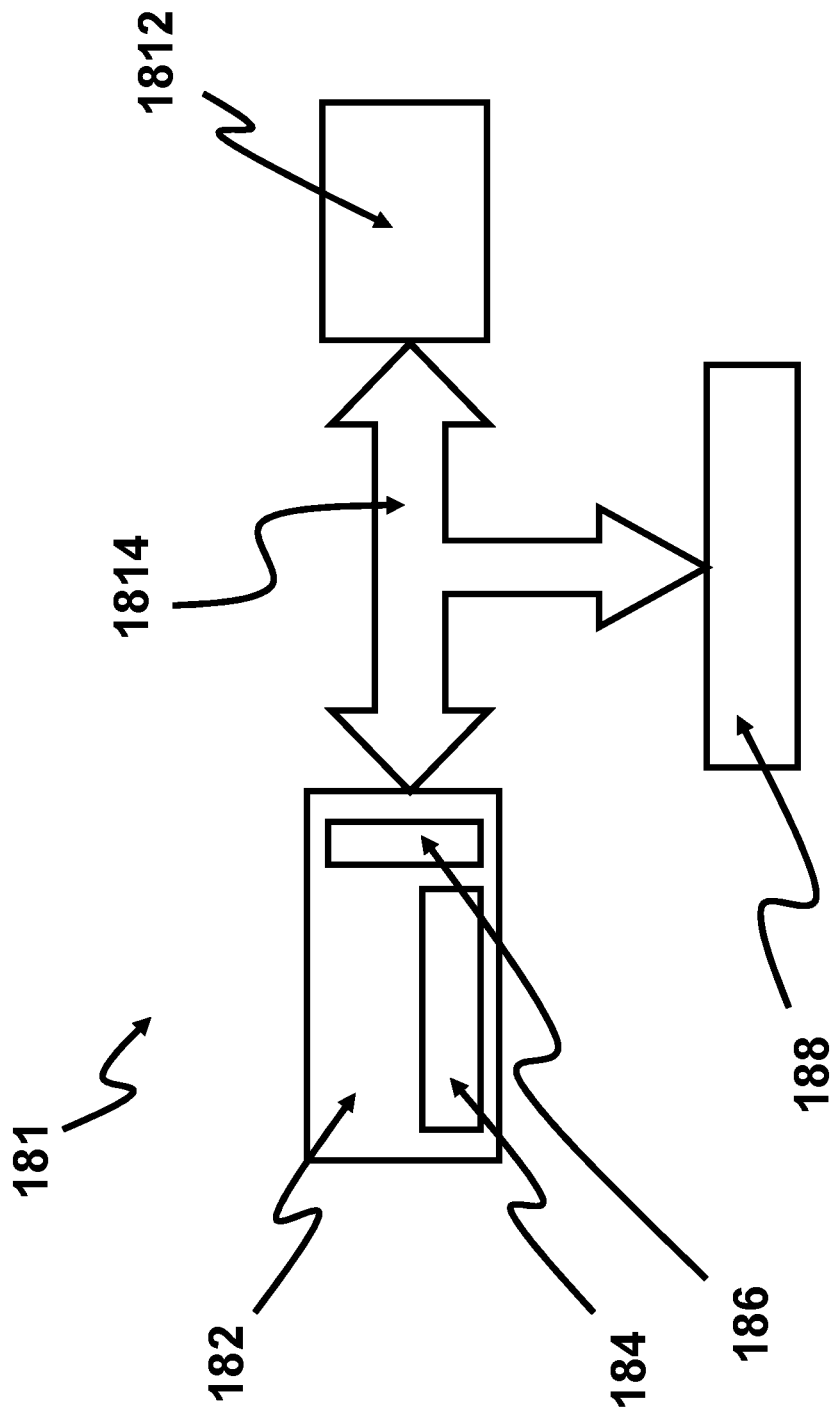
FIG. 18 shows a logical interconnection of the elements of a high integrity vision measurement and training system including security and system integrity information to ensure that the system is composed of proper elements and that they are properly interconnected.

Since the vision measurement and training system 11 provides measurements that may be used for medical diagnostic purposes, it is essential that the system be properly interconnected from elements that were intended for each purpose. This is especially critical for low cost systems that might be constructed with "off-the-shelf" components. Since common computer components are generally designed to interoperate as easily as possible, it is possible for improper systems to be constructed unless action is taken to ensure system integrity. For example, the binocular viewer 110a might be incorrectly replaced with another viewer offering lower screen resolution, that might result in poor system accuracy. In FIG. 18, a high integrity vision measurement and training system 181 is shown. Central processor 182 is connected to the other system elements through a logical interconnection 1814. Central processor 182 might be a computer, cell phone, PDA, game platform, or other central processing function. Logical interconnection 1814 might be a wired connection such as USB (Universal Serial Bus), or a wireless connection such as Bluetooth. In fact, logical interconnection 1814 might be made up of several different physical interconnects. That is, logical interconnection 1814 could be common only at a logical level and the physical interconnections to the various system blocks could be over different physical interconnections. Other system elements are also shown. Box 1812 may represent a binocular viewer, while box 188 may be a human input device. Other displays, sensor, controllers, input devices, stimulus devices may also be connected. For example, earphones 116 are shown in FIG. 1 and while not shown in FIG. 18, they could be added. Central processor 182 as shown includes a secure memory 184 and encryption interface 186. The high integrity vision measurement and training system 181 ensures system integrity by passing secure coded messages from the various system elements to the central processor 182 to ensure that the system is composed of the proper devices with all the correct and necessary software and hardware. While the system could be composed in a wide variety of ways, the preferred embodiment is for the central processor 182 to send a secure encrypted request to box 1812 requesting that it identify itself. Box 1812 then sends a response indicating its overall makeup and configuration. The response from box 1812 would normally also be encrypted to ensure that someone trying to clone the system could not easily extract the messaging scheme and generate a cloned system that may not meet the original system performance. The secure messaging between central processor 182 and the other elements (boxes) in the system might make use of a public key encryption system so that different encryption codes could be used for each operation of the system. Other secure encryptions are also possible and will not be enumerated here. Secure memory 184 would be used by central processor 182 to ensure that the specific system requirements and security codes remain intact and are not available to hackers or others with malicious intent. Encryption interface 186 would handle all encryption and decryption including passing public keys to each box (element) of the system.

Of course, many other ways to ensure that the system is properly composed of the right elements and properly configured also exist. One simple method is to use proprietary hardware interfaces between the system elements or to use conventional interfaces with proprietary connector plugs that will not interoperate with conventional plugs. However, these approaches make it difficult to interconnect off-the-shelf hardware that is readily available and perfectly adequate for use in the system. For example, it may be desirable to design the vision measurement and training system 11 so that it can work with many different human input devices to accommodate users 12b with physical handicaps or conditions that make it hard for them to operate certain devices. In this case, it is a great benefit to use conventional interfaces such as USB and ensure proper system operation and security through the public key security system explained above or other possible security systems. And, of course, some elements of the high integrity vision training and measurement system 181 may not need to be checked through a security protocol as described above if they are truly generic. It is possible that headphones, microphones and some other possible elements are sufficiently generic that available off-the-shelf components can be used interchangeably in the system without risk of unacceptable system operation.

With the security features of the high integrity vision measurement and training system 181 in place, additional benefits from system security can also be derived. For example, the user's information can be protected to ensure that privacy is respected and only those with specific permission can access databases and other information the user 12b may consider to be private. In the case of transmission of the database information to a care provider's office, for example, the public key encryption system could be used to ensure that the database is received intact and was not intercepted or maliciously corrupted. Use of PIN (Personal Identity Number) codes, passwords, firewalls and other security techniques to protect user 12b information and privacy are all possible.

From the description above, some possible advantages of certain embodiments of the disclosure are clear:

a) an automated computer system can be developed to measure and train a person's vision;

b) binocular viewer technology can be applied to create images that vary focal depth and parallax so that realistic images can be generated;

c) features and use of color can be applied to draw a user's attention to a primary image and away from images in a practical display system that cannot have the correct focal depth or parallax;

d) images can be created that are beneficial for measuring and training a users vision;

e) images can be created that allow a user to view a single stereoscopic vision image while objects of interest are included that allow vision in each eye to be assessed independently;

f) data collected through an automated vision measurement and training system can be used to control other video systems to benefit a user;

g) security techniques can be applied to the system to ensure that it is composed of the correct elements and that each element is properly connected;

h) collected data can be added to a data base and the user can be alerted if changes in their vision warrant the attention of a healthcare professional; and i) data from multiple games can be combined into a database so that the user may use different games at different times so that the vision measurement and training remains exciting, interesting and engaging.

The benefits of the disclosure should be clear. It offers a system to measure and train a user's vision. The system can be implemented with a variety of display technologies, while the use of a binocular viewer will provide very realistic images. The position and focal depth of objects in the display can be varied to create images very similar to a real world experience. In this way, the eye can be forced to focus as it would when objects at varying distances are viewed in the real world. Data for many vision conditions including retinal disorders, focusing disorders, muscular disorders and other afflictions can be measured and tracked. If a user's vision has deteriorated substantially, the user can be notified. Data from multiple measurement and training sessions and from different games can be combined. Security techniques can be applied to ensure a properly operating system.

Although the disclosure has been described in detail, those skilled in the pertinent art should understand that they can make various changes, substitutions and alterations herein without departing from the scope of the disclosure in its broadest form.

What is claimed is:

1. A binocular viewer, comprising
left and right display screens;
a variable focal depth optical subsystem located in an optical path between and separate from said display screens and a user when said user uses said binocular viewer, wherein a parallax of at least one of a plurality objects in images placed on said display screens is coordinated with a focal depth of said at least one object; and
at least one alignment device to ensure alignment of said binocular viewer.

2. The binocular viewer as recited in claim 1 wherein said at least one alignment device is selected from the group consisting of:
a head strap;
a head piece;
at least one temple pad; and
at least one nose piece.

3. A method of using a binocular viewer, comprising:
viewing left and right display screens of said binocular viewer through a variable focal depth optical subsystem associated therewith and separate therefrom, wherein a parallax of at least one of a plurality objects in images placed on said left and right display screens is coordinated with a focal depth of said at least one object; and
aligning said binocular viewer.

4. The method as recited in claim 3, wherein said aligning uses a first measurement of said user compared to a second measurement of said user to generate a signal to said user of misalignment.

5. The method as recited in claim 4 wherein said user, upon said signal of misalignment, readjusts said binocular viewer to realign said binocular viewer.

6. A binocular viewing system, comprising:
a binocular viewer having left and right display screens and a variable focal depth optical subsystem located in an optical path between and separate from said display screens and a user when said user uses said binocular viewer;
a computer configured to provide control signals to said binocular viewer operable to place images on said left and right display screens and vary a focal depth of said variable focal depth optical subsystem, said images including a plurality of objects controlled by said variable focal depth optical subsystem to make at least one of said plurality of objects appear closer to user and at least one of another of said plurality of objects appear farther away from said user, wherein a parallax of at least one of said plurality of objects is coordinated with a focal depth of said at least one object; and
at least one alignment device to ensure alignment of said binocular viewer.

7. The binocular viewing system of claim 6, wherein a perspective of at least one of said plurality of objects is coordinated with a focal depth of said at least one object.

8. The binocular viewing system of claim 6, wherein a size of at least one of said plurality of objects is coordinated with a focal depth of said at least one object.

9. The binocular viewing system of claim 6, wherein a parallax, perspective, and size of at least one of said plurality of objects is coordinated with a focal depth of said at least one object.

10. The binocular viewing system of claim 6, wherein some of said plurality of objects move so that they appear at times closer to said user and at other times appear farther away from said user.

11. The binocular view system of claim 10, wherein a parallax, perspective, size, and focal depth of said some of objects that are moving are kept approximately consistent as the said some objects move.

12. The binocular viewing system of claim 6, further comprising a human input device.

13. The binocular viewing system of claim 12 wherein said human input device is selected from the group consisting:
a keyboard;
a game controller;
a microphone;
a mouse;
a touchpad;
a foot pedal;
a steering wheel; and
a joystick.

14. The binocular viewing system of claim 12 wherein said computer sends a secure encrypted request to at least one of said binocular viewer and said human input device and, in response to said secure encrypted request, said at least one of said binocular viewer and said human input device sends back to said computer an encrypted response identifying a hardware makeup and software configuration of said at least one of said binocular.

* * * * *